US009797900B2

(12) United States Patent
Dahl et al.

(10) Patent No.: US 9,797,900 B2
(45) Date of Patent: Oct. 24, 2017

(54) MULTIPLEXED CHROMATOGRAPHY-IMMUNOASSAY METHOD FOR THE CHARACTERIZATION OF CIRCULATING IMMUNE COMPLEXES

(71) Applicant: Hoffmann-La Roche Inc., Little Falls, NJ (US)

(72) Inventors: Uwe Dahl, Penzberg (DE); Gregor Jordan, Groebenzell (DE); Roland Staack, Munich (DE)

(73) Assignee: F. HOFFMAN-LA ROCHE AG, Little Falls, NJ (US)

( * ) Notice: Subject to any disclaimer, the term of this patent is extended or adjusted under 35 U.S.C. 154(b) by 0 days.

(21) Appl. No.: 14/478,536

(22) Filed: Sep. 5, 2014

(65) Prior Publication Data

US 2015/0132781 A1 May 14, 2015

Related U.S. Application Data

(63) Continuation of application No. PCT/EP2013/054587, filed on Mar. 7, 2013.

(30) Foreign Application Priority Data

Mar. 8, 2012 (EP) .................................... 12158634

(51) Int. Cl.
| | | |
|---|---|---|
| G01N 31/00 | (2006.01) | |
| G01N 33/53 | (2006.01) | |
| G01N 33/564 | (2006.01) | |
| G01N 33/68 | (2006.01) | |
| G01N 33/94 | (2006.01) | |

(52) U.S. Cl.
CPC ......... *G01N 33/564* (2013.01); *G01N 33/686* (2013.01); *G01N 33/94* (2013.01)

(58) Field of Classification Search
CPC .............. A61K 2039/505; C07K 16/00; C07K 2317/55; C07K 2317/92
See application file for complete search history.

(56) References Cited

U.S. PATENT DOCUMENTS 8,865,417 B2 * 10/2014 Singh ................. G01N 33/5091
435/7.1

FOREIGN PATENT DOCUMENTS

| EP | 0 834 076 | | 12/1999 |
| EP | 2 354 792 | A1 | 8/2011 |
| WO | 97/00447 | | 1/1997 |
| WO | 2008/031532 | A1 | 3/2008 |
| WO | 2009/140242 | | 11/2009 |
| WO | 2011/056590 | A1 | 5/2011 |
| WO | 2012/054532 | A1 | 4/2012 |

OTHER PUBLICATIONS

Wakankar et al. (Landes Bioscience, vol. 3, No. 2, Mar./Apr. 2011, p. 161-172).*
Schellenberger et al. (Nature Biotechnology, vol. 27, No. 12, Dec. 2009, pp. 1186-1192).*
Xu et al. (Scandinavian Journal of Immunology, vol. 71, pp. 55-60, 2010) teach ELISA elution method to dissociate antibody complexes.*
Simonovska et al. (MED ARH 2011, vol. 65, No. 6., pp. 324-326) teach assays measuring circulating immune complexes and antibodies.*
Coyle, P.K. et al., "Detection and isolation of immune complexes in multiple sclerosis cerebrospinal fluid" Journal of Neuroimmunology 15:97-107 ( 1987).
Kneba, M. et al., "Chromatofocusing Combined with the ELISA Technique. A Sensitive Method for the Analysis of Immune Complexes" Journal of Immunological Methods 61:233-243 ( 1983).
Lambert, P.H. et al., "A WHO Collaborative Study for the Evaluation of Eighteen Methods for Detecting Immune Complexes in Serum" J. Clin. Lab. Immunol. 1:1-15 ( 1978).
Levinson, S.S. et al., "Methods for Measuring Circulating Immune Complexes" Clinical Immunology Newsletter 8(3):39-42 ( 1987).
Matousovic, K. et al., "IgA-containing immune complexes in the urine of IgA nephropathy patients" Nephrol Dial Transplant 21:2478-2484 ( 2006).
Rattan, B. et al., "Circulating Immune Complexes in Rabbits Surviving Rinderpest Virus Infection" Acta virologica 38:105-110 ( 1994).
Stubenrauch, K. et al., "Evaluation of a generic immunoassay with drug tolerance to detect immune complexes in serum samples from cynomolgus monkeys after administration of human antibodies" Journal of Pharmaceutical and Biomedical Analysis 52:249-254 ( 2010).
Stubenrauch, K. et al., "Generic anti-drug antibody assay with drug tolerance in serum samples from mice exposed to human antibodies" Analytical Biochemistry 430:193-199 ( 2012).
Wang et al., "Analysis of Anti-drug Antibodies (ADA) to Adalimumab in Patient Serum Using a Novel Homogeneous Mobility Shift Assay" The American journal of Gastroenterology 105( Suppl 1):S444-S445 (Oct. 2010).
Wang, S.-L. et al., "Development and validation of a homogeneous mobility shift assay for the measurement of infliximab and antibodies-to-infliximab levels in patient serum" Journal of Immunological Methods 382:177-188 ( 2012).

* cited by examiner

*Primary Examiner* — Lisa Cook
(74) *Attorney, Agent, or Firm* — Grant E. Kalinowski

(57) ABSTRACT

Thus, herein is reported a method for analyzing/characterizing circulating immune complexes (CICs) formed in vivo comprising a size-exclusion chromatography of a sample obtained from a mammal to which the drug had been administered at least once for determining the weight/size of the immune complexes, optionally a second non-SEC chromatography, and at least one immunoassay, whereby the immune complex is characterized by the correlation of the immune complex size and the immunoassay result/read-out. Also reported herein is the use of a method as reported herein for determining a correlation to altered pharmacokinetics, for determining loss or reduction of efficacy, for determining neutralization of natural counterparts of the drug, for determining immune and hypersensitivity reactions, including serum sickness/type III hypersensitivity reaction/immune complex-mediated disease.

12 Claims, 6 Drawing Sheets

ADA-Drug Assay

| 3001_t=23d | 0.554 | 0.574 | 0.839 | 1.748 | 1.874 | 1.367 | 0.933 | 0.719 | OD 1.97 | 3001 Ig + |
|---|---|---|---|---|---|---|---|---|---|---|
| 3003_t=23d | 0.125 | 0.178 | 0.210 | 0.384 | 0.740 | 1.201 | 2.016 | 1.579 | 0.51 | 3003 |
| 3104_t=23d | 0.137 | 0.174 | 0.183 | 0.246 | 0.397 | 0.735 | 1.039 | 0.905 | 0.49 | 3004 Ig ++ |

ADA Assay

| 3001_t=23d | 0.331 | 0.372 | 0.493 | 1.032 | 1.715 | 1.999 | 2.133 | 2.120 | 1.2 | 3001 Ig + |
|---|---|---|---|---|---|---|---|---|---|---|
| 3003_t=23d | 0.186 | 0.334 | 0.363 | 0.588 | 0.978 | 1.677 | 1.934 | 2.236 | 0.88 | 3003 |
| 3104_t=23d | 0.149 | 0.224 | 0.202 | 0.270 | 0.546 | 1.054 | 1.760 | 2.140 | 0.6 | 3004 Ig ++ |

FIG. 6

MULTIPLEXED CHROMATOGRAPHY-IMMUNOASSAY METHOD FOR THE CHARACTERIZATION OF CIRCULATING IMMUNE COMPLEXES

CROSS REFERENCE TO RELATED APPLICATIONS

This application is a continuation of International Application No. PCT/EP2013/054587, filed 7 Mar. 2013, and claims the benefit of priority under 35 USC §119(a) to European patent application number 12158634.1, filed 8 Mar. 2012, the disclosures of which are incorporated herein by reference in their entirety.

FIELD OF THE INVENTION

Herein is reported a method for detection and characterization (size and composition) of circulating immune complexes in biological matrices by a multi-step method comprising a size-exclusion chromatography (SEC) and an immunoassay.

BACKGROUND OF THE INVENTION

Most biotherapeutics can induce unwanted immune responses with possible consequences on safety and efficacy whereby these responses vary in frequency and severity (Buttel, I. C. et al., Biologicals 39 (2011) 100-109; COMMITTEE FOR MEDICINAL PRODUCTS FOR HUMAN USE (CHMP), EMEA Guideline on Immunogenicity Assessment of Biotechnology-derived Therapeutic Proteins).

The formation of anti-drug antibodies (ADA) might result in altered pharmacokinetics, loss or reduction of efficacy, neutralization of natural counterparts as well as general immune and hypersensitivity reactions, including serum sickness/type III hypersensitivity reaction/immune complex-mediated disease (Buttel, I. C. et al., Biologicals 39 (2011) 100-109; COMMITTEE FOR MEDICINAL PRODUCTS FOR HUMAN USE (CHMP), EMEA Guideline on Immunogenicity Assessment of Biotechnology-derived Therapeutic Proteins).

Serum sickness like syndrome, as a result of the formation of ADA-D complexes, is a well-known adverse event and has been reported for a variety of biologicals in preclinical studies (Ponce, R. et al., Regul. Toxicol. Pharmacol. 54 (2009) 164-182) and in clinical practice (COMMITTEE FOR MEDICINAL PRODUCTS FOR HUMAN USE (CHMP), EMEA Guideline on Immunogenicity Assessment of Biotechnology-derived Therapeutic Proteins; Dreyfus, D. H. et al., Ann. Allergy Asthma Immunol. 96 (2006) 624-627; Gamarra, R. M., J. Emerg. Med. 30 (2006) 41-44; Goto, S. et al., Int. J. Hematol. 89 (2009) 305-309; Hansel, T. T. et al., Nat. Rev. Drug Discov. 9 (2010) 325-338; Pilette, C. et al., J. Allergy Clin. Immunol. 120 (2007) 972-973; Tamilvanan, S. et al., J. Drug Target 18 (2010) 489-498).

For marketed drugs, the features of major reactions such as serum sickness or severe allergic reactions are diagnosed clinically. In cases where adverse events follow administration of the implicated mAb, the reactions are attributed to an antibody response (COMMITTEE FOR MEDICINAL PRODUCTS FOR HUMAN USE (CHMP), EMEA Guideline on Immunogenicity Assessment of Biotechnology-derived Therapeutic Proteins). Indeed, only very limited data can be found where the formation of ADAs was investigated and correlated with the clinically observed signals (Goto, S. et al., Int. J. Hematol. 89 (2009) 305-309).

Given the potential seriousness of immunogenicity, the EMEA emphasized the importance of confirmation and characterization of ADA formation (COMMITTEE FOR MEDICINAL PRODUCTS FOR HUMAN USE (CHMP), EMEA Guideline on Immunogenicity Assessment of Biotechnology-derived Therapeutic Proteins).

Assessment of immunogenicity is typically conducted using immunoassays which are designed to detect ADAs (Mire-Sluis, A. R. et al., J. Immunol. Methods 289 (2004) 1-16; Shankar, G. et al., J. Pharm. Biomed. Anal. 48 (2008) 1267-1281; Koren, E. et al., J. Immunol. Methods 333 (2008) 1-9).

Information of ADA incidence, however, does until now not enable a profound correlation with clinical findings and altered pharmacokinetics.

The amount and size of the formed ADA-drug complexes is dependent on several parameters, e.g. ADA and drug concentration/ratio as well as epitope and valence (Abbas, A. K. and Lichtman, A. H., Diseases caused by immunity responses: Hypersensitivity and Autoimmunity, in: Saunders (2003); Murphy, K. et al., Janeway's Immunobiology, in: Garland Science, Taylor & Francis Group, LLC (2008)).

The complex size and charge is an important determinant of complex clearance or induction of adverse events. Typically, larger complexes are cleared by the reticulo-endothelial system, small complexes usually do not trigger inflammation, whereas intermediate size complexes may fix complement and can cause tissue damage (Abbas, A. K. and Lichtman, A. H., Diseases caused by immunity responses: Hypersensitivity and Autoimmunity, in: Saunders (2003); Murphy, K. et al., Janeway's Immunobiology, in: Garland Science, Taylor & Francis Group, LLC (2008); Mannik, M., Serum Sickness and pathophysiology of immune complexes, in: Clinical Immunology: Principles and Practices, Rich R. R., Fleisher T. A. S. B. D., Shearer W. T., Strober W. (eds.) 1062-1071 (1996); Sicherer, S. H., Leung D. Y. M., Serum Sickness, in: Nelsons textbook of pediatrics, Kliegman R. M., Behrman R. E., Jenson H. B. J., Stanton B. F. (eds.), Saunders Elsevier, pp. 985-986 (2007). Furthermore, charge of the complexes is an important factor for tissue deposition of the complexes (Abbas, A. K. and Lichtman, A. H., Diseases caused by immunity responses: Hypersensitivity and Autoimmunity, in: Saunders (2003); Mannik, M., Serum Sickness and pathophysiology of immune complexes, in: Clinical Immunology: Principles and Practices, Rich R. R., Fleisher T. A. S. B. D., Shearer W. T., Strober W. (eds.) 1062-1071 (1996)).

For a profound evaluation of an ADA response, potentially formed ADA-drug complexes should be characterized with regard to size and charge. In addition, if an endogenous counterpart of the drug exists, information of whether the formed ADAs are cross-reactive to these molecules and whether endogenous counterparts are also part of the complex is a valuable information. Furthermore, structural characterization of the antigen/drug in the immune complexes provides information for the pathogenesis.

Coyle et al. report the detection and isolation of immune complexes in multiple sclerosis cerebrospinal fluid (Journal of Neuroimmunology 15 (1987) 97-107). Chromatofocusing combined with the ELISA technique—a sensitive method for the analysis of immune complexes is reported by Kneba, M., et al. (J. Immunol. Meth. 61 (1983) 233-243). Matousovic, K., et al. report IgA-containing immune complexes in the urine of IgA nephropathy patients (Nephrology Dialysis Transplantation 21 (2006) 2478-2484). Circulating immune complexes in rabbits surviving rinderpest virus infection is reported by Rattan, B., et al. (Acta Vir. 38 (1994) 105-110). In WO 2008/031532 an anti-drug antibody assay is reported. Stubenrauch, K., et al., report the evaluation of a generic immunoassay with drug tolerance to detect immune complexes in serum samples from cynomolgus monkeys after administration of human antibodies (J. Pharm. Biomed. Anal. 52 (2010) 249-254). In WO 2011/056590 assays for the detection of anti-TNF drugs and autoantibodies is reported. Wang Shui Long et al. report the analysis of anti-drug antibodies (ADA) to Adalimumab in patient serum using a novel homogeneous mobility shift assay (Am. J. Gastroent. 105 (Sup 1, 2010) S444-S445. In EP 2 354 792 a method for detecting anti-drug antibodies is reported. Lambert, P. H., et al. report a WHO collaborative study for the evaluation of eighteen methods for detecting immune complexes in serum (J. Clin. Lab. Immunol. 1 (1978) 1-15). Methods for measuring circulating immune complexes are reported by Levinson, S. S. et al. (Clin. Immunol. Newsletter 3 (1987) 39-42).

SUMMARY OF THE INVENTION

It has been found that with a method for detection and characterization (size and composition) of circulating immune complexes, e.g. complexes containing ADAs against a given drug, in biological matrices comprising a multi-step method using size-exclusion chromatography (SEC) in combination with at least one immunoassay, a correlation to altered pharmacokinetics, loss or reduction of efficacy, neutralization of natural counterparts as well as general immune and hypersensitivity reactions, including serum sickness/type III hypersensitivity reaction/immune complex-mediated disease can be made.

One aspect as reported herein is a method for analyzing/characterizing a circulating immune complex (CIC) formed in vivo comprising
  a) a size-exclusion chromatography of a sample obtained from a mammal to which a drug had been administered at least once for determining the weight/size of the immune complex,
  b) optionally a second non-SEC chromatography,
  c) at least one immunoassay, and
  d) optionally a mass-spectrometry-based analysis,
whereby the immune complex is characterized by the correlation of the immune complex size and the immunoassay or mass-spectrometry assay result/read-out.

One aspect as reported herein is a method for analyzing determining a circulating complexed anti-drug antibody immune complex comprising a (exogenous) therapeutic polypeptide and an endogenous anti-drug antibody formed in vivo comprising
  a) a size-exclusion chromatography of a sample obtained from a mammal to which a drug had been administered at least once for determining the weight/size of the immune complex,
  b) optionally a second non-SEC chromatography,
  c) at least one heterogeneous immunoassay for detecting the anti-drug antibody, and
  d) and optionally a mass-spectrometry-based analysis,
whereby the immune complex is characterized by the correlation of immune complex size and immunoassay or mass-spectrometry assay read-out/result,
whereby the therapeutic polypeptide is a synthetic or not-naturally occurring therapeutic polypeptide.

In one embodiment of all aspects the sample is serum or cerebrospinal fluid.

In one embodiment of all aspects the immune complex is a drug-specific immune complex.

A drug specific immune complex comprises the drug together with other non-drug molecules.

In one embodiment of all aspects the immunoassay is selected from the group comprising anti-drug antibody detection assay, drug-neutralizing antibody detection assay, pharmacokinetic assay (drug quantification assay), antibody isotyping assay, assay for determining ADA-cross-reactivity to endogenous drug counterpart (if the drug comprises a part that also occurs endogenously in the mammal), complement binding assay (bound complement or binding capacity for complement), assay for determining endogenous counterpart of the drug comprised in an immune complex (if the drug comprises a part that also occurs endogenously in the mammal).

In one embodiment of all aspects the immunoassay is a homogeneous immunoassay or a heterogeneous immuno assay. In one embodiment the immunoassay is a radio immunoassay (RIA), or an enzyme immunoassay (EIA, ELISA, EMIT), or an fluorescence polarization immunoassay (FPIA), or an luminescence immunoassay (LIA), or an immuno radiometric immunoassay (IRMA), or a microbead-enzyme immunoassay (MEIA), or an enzyme-linked fluorescence assay (ELFA), or a lectin-enzyme immunoassay (LEIA), or an immunofluorescence assay (IFA), or an electrochemiluminescense assay (ECLIA), or an immunomagnetic electrochemiluminescense assay (IMECL), or an chemiluminescence dot-immunobinding assay (CDIA), or a turbidity assay, or an particle-enhanced immunoturbidimetric assay. In one embodiment the immunoassay is an enzyme linked immunosorbent assay (ELISA), or an electrochemiluminescense assay (ECLIA), or a chemiluminescence dot-immunobinding assay (CDIA), or a fluorescence polarization immunoassay (FPIA), or a turbidity assay, or a particle-enhanced immunoturbidimetric assay.

In one embodiment of all aspects the second non-SEC chromatography is an ion exchange chromatograph (cation- or anion exchange chromatography), or a reversed phase chromatography, or a hydrophilic interaction chromatography (HILIC), or a hydrophobic interaction chromatography (HIC), or a hydrophobic charge interaction chromatography (HCIC), or a restricted access material chromatography (RAMC).

In one embodiment of all aspects the size-exclusion chromatography is a size-exclusion chromatography with collection of the eluate in fractions. In one embodiment each of the fractions is analyzed in the immunoassay.

In one embodiment of all aspects least one of the fractions of the size-exclusion chromatography is further separated by a second non-SEC chromatography with collection of the eluate in aliquots. In one embodiment each of the fractions is analyzed in the immunoassay. In one embodiment each of the fractions of the size-exclusion chromatography are analyzed by the second non-SEC chromatography.

In one embodiment of all aspects the fraction is an aliquot.

In one embodiment of all aspects the immunoassay is an enzyme linked immunosorbent assay.

In one embodiment of all aspects the at least one immunoassay is one, or two, or three, or four, or five, or six immunoassays.

In one embodiment of all aspects the immunoassay is an anti-drug antibody immunoassay.

In one embodiment of all aspects at least one of the immunoassays is a bridging enzyme linked immunosorbent assay.

A positive bridging enzyme linked immunosorbent assay denotes that the anti-drug antibody was part of an ADA-D complex. The detection of an anti-drug antibody in higher molecular weight fraction, i.e. in earlier eluting fractions of the size exclusion chromatography, denotes that the anti-drug antibody was part of a higher molecular weight complex.

In one embodiment of all aspects at least one of the enzyme linked immunosorbent assays is a complex assay for the detection of ADA-D complexes. In one embodiment the complex assay comprises a drug specific capture antibody and an anti-species specific antibody as detection antibody.

In one embodiment of all aspects at least one of the immunoassays is a direct assay for the detection of anti-drug antibodies which are bound to the drug and/or to the endogenous counterpart of the drug. In one embodiment the direct assay comprises as capture molecule immobilized drug or endogenous counterpart of the drug and an anti-species specific antibody as detection antibody.

The direct assay employs the establishment of an equilibrium of anti-drug antibody binding to drug and/or endogenous counterpart in a sample and immobilized drug, after free anti-drug antibody has been removed by the size exclusion chromatography.

In one embodiment of all aspects the drug surface coating is a dense drug surface coating.

By the dense surface coating very the shift of the equilibrium towards the binding to the surface bound drug is effected (using avidity of the anti-drug antibody).

In one embodiment of all aspects the sample is incubated in the immunoassay for a time period of from 16 to 32 hours.

One aspect as reported herein is a method for separation of drug from ADA-D complexes in order to increase the drug tolerance of succeeding ADA assays/immunoassays. Likewise the methods as reported herein can be used to increase the drug tolerance of immunoassays.

One aspect as reported herein is a method for the characterization of anti-drug antibody-drug (ADA-D) complexes formed in vivo comprises
  a) a size-exclusion chromatography of a sample obtained from a mammal to which the drug had been administered at least once for determining the weight/size of the ADA-D complexes,
  b) at least one enzyme linked immunosorbent assay for the detection of anti-drug antibodies,
  whereby the immune complex is characterized to be
  a low molecular weight complex by a positive enzyme linked immunosorbent assay and a weight between about 150 kDa and about 400 kDa,
  a medium molecular weight complex by a positive enzyme linked immunosorbent assay and a weight between about 400 kDa and about 1,500 kDa, or
  a high molecular weight complex by a positive enzyme linked immunosorbent assay and a weight between about 1,500 kDa and about 7,000 kDa.

One aspect as reported herein is the use of a method as reported herein for correlation of immune complex characteristics to altered pharmacokinetics.

One aspect as reported herein is the use of a method as reported herein for determining reduction of efficacy of a drug.

One aspect as reported herein is the use of a method as reported herein for determining neutralization of natural counterparts of the drug.

One aspect as reported herein is the use of a method as reported herein for determining immune and hypersensitivity reactions against the drug.

One aspect as reported herein is the use of a method as reported herein for determining IgG glomeruli deposit.

In one embodiment of all aspects the immune and hypersensitivity reaction is a serum sickness/type III hypersensitivity reaction/immune complex-mediated disease.

One aspect as reported herein is the use of a method as reported herein for determining the presence of autoimmune antibody comprising immune complexes.

One aspect as reported herein is the use claim of a method as reported herein for determining the presence of modified/complexed drug.

In one embodiment of all aspects the drug is a human or humanized antibody.

BRIEF DESCRIPTION OF THE FIGURES

FIG. 6 IgG deposit positive animals (semi quantitative evaluation).

DETAILED DESCRIPTION OF THE INVENTION

Definitions

Figure 1:
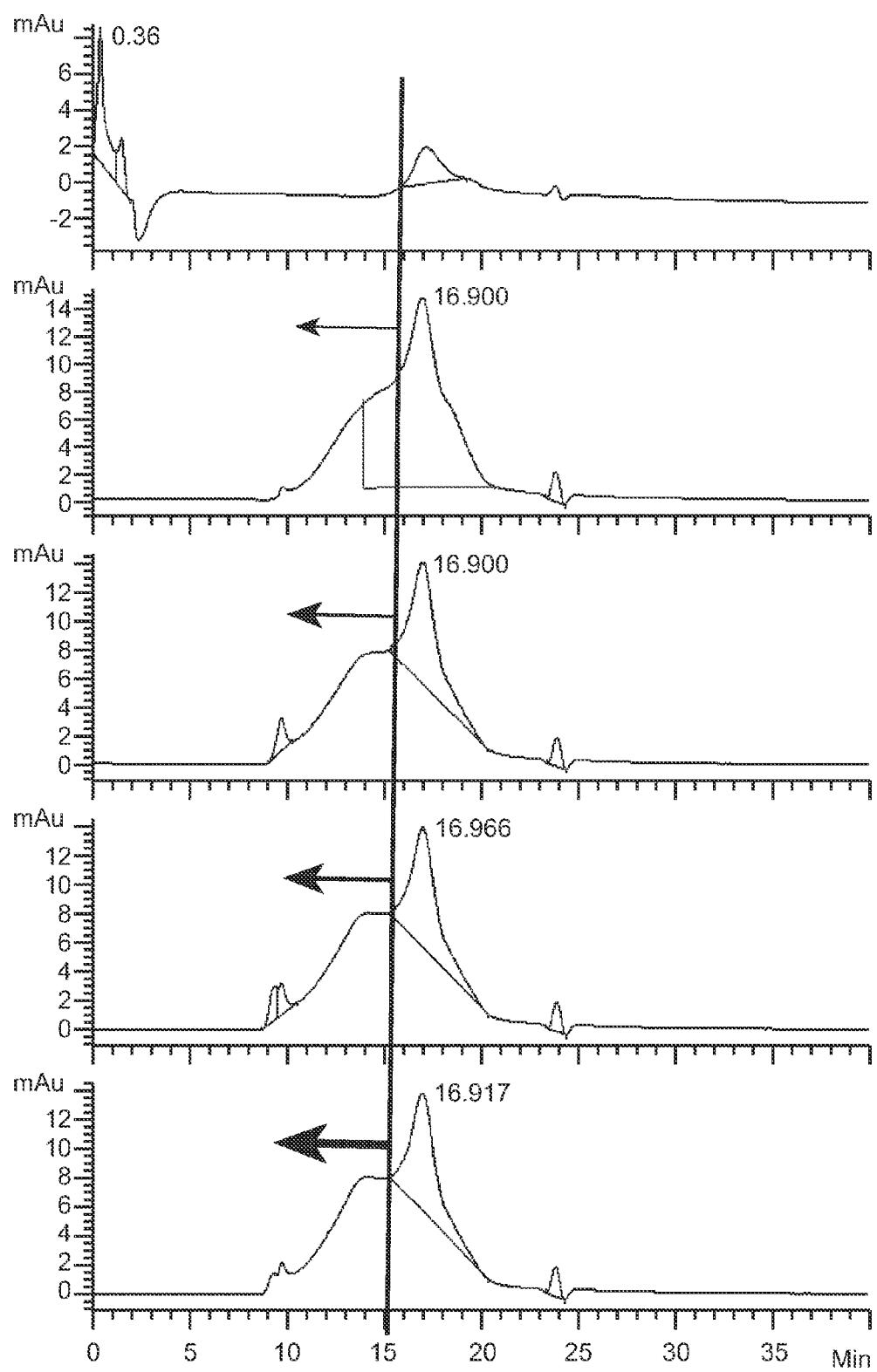
FIG. 1 Kinetic of a drug ADA-D complex formation (1 mg drug and 1 mg ADA).

The term "anti-drug antibody" denotes an antibody, which is directed against an antigenic region of the drug. This antigenic region may be an antigenic amino acid sequence of the drug, or the glycostructure of the drug. In one embodiment the anti-drug antibody is directed against a secondary modification of the drug resulting from the recombinant production of said drug antibody in non-human cells, such as, CHO cells, HEK cells, or BHK cells. Generally anti-drug antibodies are directed against an antigenic region of a drug that is recognized by the immune system of an animal to which the drug is administered. Such an anti-drug antibody is a "specific anti-drug antibody". Drugs are designed to comprise as few as possible antigenic regions. For example, drugs intended for the use in humans can be humanized prior to the application to a human patient in order to minimize the generation of an immune response against the drug. This immune response would be in the form of anti-drug antibodies which are directed against the non-human parts of such a humanized drug (see e.g. Pan, Y., et al., FASEB J. 9 (1995) 43-49).

The term "chromogens" denotes fluorescent or luminescent groups and dyes.

The term "detectable label" denotes enzymes, NMR-active groups or metal particles, haptens, such as, e.g., digoxigenin. The detectable label can also be a photoactivatable crosslinking group, e.g. an azido or an azirine group. Metal chelates which can be detected by electrochemiluminescence are also preferred signal-emitting groups, with particular preference being given to ruthenium chelates, e.g. a ruthenium (bispyridyl)$_3^{2+}$ chelate. Suitable ruthenium labeling groups are described, for example, in EP 0 580 979, WO 90/05301, WO 90/11511, and WO 92/14138.

The term "drug" denotes a polypeptide, such an antibody or a non-antibody molecule, which can be administered to an individual for the treatment of a disease. Drugs (such as therapeutic polypeptides or therapeutic monoclonal antibodies) are being used widely for the treatment of various diseases such as oncological diseases (e.g. hematological and solid malignancies including non-Hodgkin's lymphoma, breast cancer, and colorectal cancer), immunological diseases, central nervous diseases, vascular diseases, or infectious diseases. Such drugs are described, for example, by Levine, A. P. et al., Journal of the Royal Society of Medicine 98 (2005) 145-152. Such drugs are, for instance, antibodies against CD20, CD22, HLA-DR, CD33, CD52, EGFR, G250, GD3, HER2, PSMA, CD56, VEGF, VEGF2, CEA, Levis Y antigen, IL-6 receptor, or IGF-1 receptor. Therapeutic antibodies are also described by Groner, B., et al., Curr. Mol. Meth. 4 (2004) 539-547; and Harris, M., Lancet Oncol. 5 (2004) 292-302.

The term "mammal" denotes a living being belonging to the class of vertebrate animals. The term mammal denotes in one embodiment primates, cats, dogs, sheep, rats, mice, and rabbits. In one embodiment the term mammal denotes the members of the families of the order of primates comprising marmosets and tamarins (family Callitrichidae), new world monkeys (family Cebidae), old world monkeys (family Cercopithecidae), dwarf and mouse lemurs (family Cheirogaleidae), aye-aye (family Daubentoniidae), bushbabies and galagos (family Galagonidae), gibbons and lesser apes (family Hylobatidae), indris, sifakas, and relatives (family Indridae), true lemurs (family Lemuridae), lorises (family Loridae), sportive lemurs (family Megaladapidae), tarsiers (family Tarsiidae), as well as crossings thereof. In one embodiment the mammal is selected from the group comprising the members of the families of marmosets and tamarins, old world monkeys, dwarf and mouse lemurs, gibbons and lesser apes, true lemurs, as well as crossings thereof. In this specific embodiment the closest relatives to mankind, the great apes, especially the group of chimpanzees, bonobos, gorillas and orangutans is excluded.

The term "sample" denotes any quantity of a substance from a mammal to which a drug has been administered. Such substances include, but are not limited to, whole blood, serum, or plasma from such a mammal, which are the most widely used sources of sample in preclinical routine. In one embodiment the sample is a liquid sample like saliva, urine, synovial fluid, whole blood, plasma, or serum. In one embodiment the sample is whole blood, plasma, or serum.

The term "solid phase" means a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes, or other spectrometer sample containers. A solid phase component of an assay is distinguished from inert solid surfaces with which the assay may be in contact in that a "solid phase" contains at least one moiety on its surface, which is intended to interact with the capture antibody. A solid phase may be a stationary component, such as a tube, strip, cuvette, or microtiter plate, or may be a non-stationary component, such as beads and microparticles. Microparticles can also be used as a solid phase for homogeneous assay formats. A variety of microparticles that allow either non-covalent or covalent attachment of polypeptides and other substances may be used. Such particles include polymer particles such as polystyrene and poly (methylmethacrylate); gold particles such as gold nanoparticles and gold colloids; and ceramic particles such as silica, glass, and metal oxide particles. See for example Martin, C. R., et al., Analytical Chemistry-News & Features, May 1, 1998, 322A-327A, which is incorporated herein by reference.

Multiplexed Immune Complex Analysis Method

It has been found that with a method for the detection and characterization (size and composition) of immune complexes directed against an administered drug in a biological matrix comprising a multi-step method using size-exclusion chromatography (SEC) in combination with an immunoassay, a correlation to altered pharmacokinetics, loss or reduction of efficacy, neutralization of natural counterparts as well as general immune and hypersensitivity reactions, including serum sickness/type III hypersensitivity reaction/immune complex-mediated disease can be made.

Thus, herein is reported as one aspect a method for analyzing/characterizing circulating immune complexes (CICs) formed in vivo comprising a size-exclusion chromatography of a sample obtained from a mammal to which the drug had been administered at least once for determining the weight/size of the immune complexes, optionally a second non-SEC chromatography, and at least one immunoassay, whereby the immune complex is characterized by the correlation of the immune complex size and the immunoassay result/read-out.

It is further reported herein as one aspect a method for the characterization of anti-drug antibody-drug (ADA-D) complexes formed in vivo comprising a size-exclusion chromatography of a sample obtained from a mammal to which the drug had been administered at least once for determining the weight/size of the ADA-D complexes, and at least one enzyme linked immunosorbent assay for the detection of anti-drug antibodies, whereby the immune complex is characterized to be a low molecular weight complex by a positive enzyme linked immunosorbent assay and a weight between about 150 kDa and about 400 kDa, to be a medium molecular weight complex by a positive enzyme linked immunosorbent assay and a weight between about 400 kDa and about 1,500 kDa, or to be a high molecular weight complex by a positive enzyme linked immunosorbent assay and a weight between about 1,500 kDa and about 7,000 kDa.

Also reported herein is the use of a method as reported herein for determining a correlation to altered pharmacokinetics, for determining loss or reduction of efficacy, for determining neutralization of natural counterparts of the drug, for determining immune and hypersensitivity reactions, including serum sickness/type III hypersensitivity reaction/immune complex-mediated disease.

For example, after the administration of a drug to a mammal the immune system of the mammal may recognize the administered drug as foreign and produce anti-drug antibodies in order to neutralize the administered foreign substance. If the drug comprises elements endogenous to the mammal the anti-drug antibodies may also be directed against this element of the drug and likewise also target the endogenous counterpart in the mammal.

An immune response/ADA formation/complement activation against an administered therapeutic drug might lead to the formation of immune complexes. The formation of immune complexes (ADA-D complexes) might result in altered pharmacokinetic properties or clinical sequelae, e.g. serum sickness like syndromes.

The immune complex properties can be important determinants of induced follow-up effects:
- complex size
  - The formation of large size complexes may lead to enhanced clearance by RES system.
  - The formation of intermediate size complexes may lead to complement fixation, followed by tissue deposition and "serum sickness"
  - The formation of small size complexes may have "no" profound effect.
- complex charge
  - Cationic immune complexes can be deposited/associated with cell/tissue membranes (anionic cell surface).
- complex polarity
- C1q—bound or binding capacity Thus, thorough immune complex characterization is a prerequisite for correlation with in vivo effects (pharmacokinetic changes and/or toxicological effects).

Sole information of e.g. an anti-drug antibody (ADA) incidence, however, does not enable a profound correlation with clinical findings and altered pharmacokinetics.

The amount and size of the formed immune complexes, such as anti-drug antibody-drug complexes (ADA-D complexes), is dependent on several parameters, e.g. concentration/ratios as well as epitope and valence.

The complex size is an important determinant of complex clearance or induction of adverse events. Typically, larger complexes are cleared by the reticulo endothelial system, small complexes usually don't trigger inflammation, whereas intermediate size complexes may fix complement and can cause tissue damage.

For a profound evaluation of an immune response, potentially formed immune complexes should be characterized with regard to size. In addition, if an endogenous counterpart of the drug exists, e.g. information of whether the formed ADAs are cross-reactive to these molecules and whether endogenous counterparts are also part of the immune complex is a valuable information.

Information can be correlated with findings such as altered pharmacokinetics or adverse events due to immune formation and might provide additional information to explain differences, e.g. between immune complex positive subjects without any impact and immune complex positive subjects with altered pharmacokinetic or clinical sequelae or serum sickness like syndromes in only some immune complex positive subjects.

In order to determine the formation of immune complexes in a mammal to which a drug has been administered and in order to characterize the immune complexes formed a two-step method is required.

The method as reported herein can be used for the characterization of any immune complex, e.g. of ADA-D complexes as well as autoimmune complexes (autoimmune diseases, such as rheumatoid arthritis, lupus etc.).

Size Exclusion Chromatography

In the first step the formed immune complexes are separated with respect to their size in order to determine the apparent number of components in the complex. This can be done by size exclusion chromatography (SEC) and fractionation (in one embodiment aliquotation) of the eluate.

Assuming that an anti-drug antibody is of the IgG class it has a molecular weight of about 150 kDa and that the molecular weight of therapeutic polypeptides ranges between about 2.5 kDa (polypeptide drug; polypeptide consisting of 20 amino acid residues) and about 250 kDa (drug antibody; full length therapeutic antibody of the IgG class comprising additional fused effector polypeptides or multispecific antibody) a 1:1 stoichiometric complex of an anti-drug antibody and a drug has at least a molecular weight of about 150 kDa in case of a small polypeptide drug and up to about 400 kDa in case of a complex drug antibody.

Selection of the fractionation times defines the resolution of the size information.

The sample (bio-matrix) which can be serum plasma (e.g. for anti-drug antibody detection) or synovial fluid (such as in rheumatoid diseases) is fractionated using size exclusion chromatography. The size exclusion chromatography provides for the first information: the analyte (complex) size.

The individual fractions of the size exclusion chromatography can be analyzed using a second dimension chromatography such as IEC separation to determine the charge of the complex or reversed phase (RP) chromatography or HILIC separation to determine the polarity of the complex.

Also the individual fractions of the size exclusion chromatography can be analyzed for complement binding activity.

Also the individual fractions of the size exclusion chromatography can be analyzed using an enzyme linked immunosorbent assay (ELISA).

Enzyme Linked Immunosorbent Assay

Fractionation of the size exclusion chromatography eluate enables multiplexing of the SEC analysis as different immunoassays can be performed to determine different complexes, such as
- bridging-type-ELISA ("classical ADA screening assay): detection of ADA in higher molecular weight fraction indicates that ADA was part of a higher molecular fraction
- complex-type-assay: detection of ADA-D complexes using drug specific capture and anti-species detection is a generic approach for mAbs in preclinical studies (see e.g. WO 2006/066912, WO 2008/031532 both incorporated herein by reference)
- direct-type-assay: detection of ADAs which were bound to drug and/or to endogenous counterpart by using immobilized drug and anti-species specific detection In one embodiment for each assay a specific cut point is evaluated by analysis of blank or ideally pre-dose samples.

For cut point definition and for semi quantitative result comparison between different plates, ELISA signal should be read-out after a defined time (in one embodiment monitored by use of a positive control on the MTP).

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates (in: "Practice and theory of enzyme immunoassays", Burdon, R. H. and v. Knippenberg, P. H. (eds.), Elsevier, Amsterdam (1990) pp. 221-278) and various volumes of "Methods in Enzymology", Colowick, S. P. and Caplan, N. O. (eds.), Academic Press, dealing with immunological detection methods, especially volumes 70, 73, 74, 84, 92, and 121).

The principles of different immunoassays are described, for example, by Hage, D. S., in Anal. Chem. 71 (1999) 294R-304R. Lu, B., et al., in Analyst. 121 (1996) 29R-32R, report the orientated immobilization of antibodies for the use in immunoassays. Avidin-biotin-mediated immunoassays are reported, for example, by Wilchek, M. and Bayer, E. A., Methods Enzymol. 184 (1990) 467-469.

In the second step the size separated complexes are characterized based on their composition, e.g. the presence of anti-drug antibodies is confirmed and the specificity of the anti-drug antibodies is determined. In one embodiment the second step comprises at least one enzyme linked immunosorbent assay (ELISA).

In general an ELISA comprises a capture molecule and a tracer molecule. The capture molecule is in general immobilized/bound to a solid phase. The tracer molecule is in general conjugated to a detectable label, whereby the detectable label can either be a direct detectable label or an indirect detectable label.

For the determination of the presence of an anti-drug antibody different ELISA formats can be used:

sandwich-ELISA
  In one embodiment the drug conjugated to a solid phase is used as capture molecule and the drug conjugated to a detectable label is used as tracer molecule.
  In the sandwich-ELISA the anti-drug antibody forms a bridge between the capture molecule and the tracer molecule due to its bivalent structure. This assay format can also be termed bridging-ELISA.
  By using a sandwich-/bridging-ELISA anti-drug antibodies can be detected. Detection of an ADA in SEC fraction covering a mass range different from its molecular mass (e.g. different from about 300 kDa for IgG-IgG complex) indicates that the ADA was part of a higher molecular weight complex.

complex-type-ELISA
  In one embodiment a drug specific antibody is used as capture molecule and an anti-species specific antibody antibody conjugated to a detectable label is used as tracer molecule.
  In one embodiment the drug conjugated to a solid phase is used as capture molecule and an anti-species specific antibody antibody conjugated to a detectable label is used as tracer molecule.
  In one embodiment an anti-species specific antibody antibody conjugated to a solid phase is used as capture molecule and the drug conjugated to a detectable label is used as tracer molecule.
  In one embodiment an anti-species specific antibody antibody conjugated to a solid phase is used as capture molecule and a drug specific antibody conjugated to a detectable label is used as tracer molecule.
  In a complex-type-ELISA anti-drug antibody-drug complexes can be detected.
  In preclinical sample analysis a drug specific capture antibody and anti-species specific detection antibody can be used.
  In clinical sample analysis a drug specific capture molecule, such as an anti-idiotypic antibody, and an anti-species specific detection antibody can be used.
  This assay provides the information whether the ADA is bound to the drug or not. This is achieved by using different components of the ADA-D complex for the capturing of the complex (either via interaction with the drug or the anti-drug antibody) and for the detection of the captured complex (either via specific interaction with the anti-drug antibody in case the interaction with the drug has been used for the capturing of the complex or via specific interaction with the drug in case the anti-drug antibody has been used for the capturing of the complex).
  As the anti-drug antibody is in general a full length antibody produced by the mammal to which the drug has been administered the anti-drug antibody comprises a constant region specific for the mammal.
  Therefore, species specific antibodies can be used for the specific binding (capturing or detection) of the anti-drug antibody irrespective of the binding specificity of the anti-drug antibody exploiting the presence of a species specific constant region.

direct-type-ELISA
  In one embodiment the drug conjugated to a solid phase is used as capture molecule and an anti-species specific antibody antibody conjugated to a detectable label is used as tracer molecule.
  In one embodiment the endogenous counterpart of the drug conjugated to a solid phase is used as capture molecule and an anti-species specific antibody antibody conjugated to a detectable label is used as tracer molecule.
  By using a direct-type-ELISA comprising immobilized endogenous counterpart of the drug and anti-species antibodies for detection anti-drug antibodies can be detected and specified whether the ADA binds to the drug or the endogenous counterpart. Additionally it is possible to determine the antibody isotype of the anti-drug antibody by using species and subtype specific antibodies.

The evaluation of the results is done be a signal vs. size matrix.

In one embodiment the sample is incubated with the capture molecule and/or the tracer molecule for a time period of from 16 hours to 32 hours.

The bridging-type-ELISA is a method for the immunological determination of an immune complex of a drug (D) and an antibody against the drug (anti-drug antibody, ADA) in a sample of a mammal using a double antigen bridging immunoassay.

The immune complex is further abbreviated as ADA-D complex.

In one embodiment the immunological determination of an ADA-D complex in a sample uses a double antigen bridging immunoassay comprising a capture antibody and a tracer antibody, characterized in that one of the antibodies is an antibody that specifically binds to the Ig of the mammal and the other antibody is an antibody that specifically binds to the drug.

In the course of the determination a complex is formed between the anti-mammal Ig antibody, ADA-D complex, and anti-drug antibody and the amount of the complex formed is correlated to the concentration of the ADA-D complex, drug and/or ADA.

In one embodiment a direct sample analysis for detection of formed ADA-D complex can be performed. In such an assay positive signals are only found if the sample contains both drug and anti-drug antibodies.

In one embodiment the sample analysis is performed after pre-incubation of the sample with a predetermined amount of the drug antibody. In such an assay positive signals are found if the sample contains anti-drug antibodies independent of the presence/absence of drug in the sample.

In one embodiment the conjugation of the drug to its conjugation partner is performed by chemically binding via N-terminal and/or $\epsilon$-amino groups (lysine), $\epsilon$-amino groups of different lysins, carboxy-, sulfhydryl-, hydroxyl- and/or phenolic functional groups of the amino acid backbone of the drug and/or sugar alcohol groups of the carbohydrate structure of the drug.

In one embodiment the capture antibody or the drug is conjugated to a solid phase by passive adsorption and is therefore conjugated to the solid phase at least two different antibody sites. Passive adsorption is, e.g., described by Butler, J. E., in "Solid Phases in Immunoassay", page 205-225; Diamandis, E. P. and Christopoulos, T. K. (Editors): Immunoassays (1996) Academic Press San Diego.

In one embodiment the capture antibody or the drug is immobilized via a specific binding pair. Such a binding pair (first component/second component) is, for example, streptavidin or avidin/biotin, antibody/antigen (see, for example, Hermanson, G. T., et al., Bioconjugate Techniques, Academic Press, 1996), lectin/polysaccharide, steroid/steroid binding protein, hormone/hormone receptor, enzyme/substrate, IgG/Protein A and/or G, etc. In one embodiment the capture antibody or the drug is conjugated to biotin and immobilization is performed via immobilized avidin or streptavidin.

In one embodiment the tracer antibody is conjugated to a detectable label. In one embodiment the tracer antibody is conjugated via a specific binding pair. Such a binding pair (first component/second component) is, for example, streptavidin or avidin/biotin, antibody/antigen (see, for example, Hermanson, G. T., et al., Bioconjugate Techniques, Academic Press, 1996), lectin/polysaccharide, steroid/steroid binding protein, hormone/hormone receptor, enzyme/substrate, IgG/Protein A and/or G, etc. In one embodiment the tracer antibody is conjugated via digoxigenin and an antibody against digoxigenin to the detectable label. Alternatively the tracer antibody is conjugated to an electrochemiluminescent label, like a ruthenium bispyridyl complex.

In one embodiment the method is for the immunological determination of an antibody against a drug (anti-drug antibody, ADA) in a sample of a monkey species using a double antigen bridging immunoassay.

In one embodiment the method is for the immunological determination of an ADA in a sample of a mammal using a double antigen bridging immunoassay comprising a capture molecule and a tracer molecule, characterized in that either the capture molecule or the tracer molecule is an antibody that specifically binds to the IgG of the mammal and the respective other molecule is the drug.

In one embodiment of the immunological determination of an ADA, the capture molecule is the drug and the tracer molecule is an anti-mammal IgG antibody that specifically binds to the IgG of the mammal from which the sample is derived/obtained. In one embodiment of the immunological determination of an ADA, the capture molecule is an anti-mammal IgG antibody that specifically binds to the IgG of the mammal from which the sample is derived/obtained, and the tracer molecule is the drug. In the course of the determination a complex is formed between the drug, ADA, and anti-mammal IgG antibody and the amount of complex formed is correlated to the concentration of ADA. In one embodiment of the immunological determination of an ADA, the anti-mammal IgG antibody is a monoclonal antibody (anti-mammal IgG mAb).

Polypeptides, such as drug polypeptides or drug antibodies, contain a number of reactive moieties, such as, for example, amino groups (lysins, alpha-amino groups), thiol groups (cystins, cysteine, and methionine), carboxylic acid groups (aspartic acid, glutamic acid) and sugar-alcoholic groups. These can be employed for coupling to a binding partner like a surface, a protein, a polymer (such as e.g. PEG, Cellulose or Polystyrol), an enzyme, or a member of a binding pair (see e.g. Aslam M., and Dent, A., Bioconjuation MacMillan Ref. Ltd. (1999) 50-100).

One of the most common reactive groups of polypeptides is the aliphatic $\epsilon$-amine of the amino acid lysine. In general, nearly all polypeptides contain abundant lysine. Lysine amines are reasonably good nucleophiles above pH 8.0 (pKa=9.18) and therefore react easily and cleanly with a variety of reagents to form stable bonds. Another common reactive group in polypeptides is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, polypeptides with these groups often exist with them in their oxidized form as disulfide groups or disulfide bonds. In addition to cystine and cysteine, some polypeptides also have the amino acid methionine, which is containing sulfur in a thioether linkage. The literature reports the use of several thiolating crosslinking reagents such as Traut's reagent (2-iminothiolane), succinimidyl (acetylthio) acetate (SATA), or sulfosuccinimidyl 6-[3-(2-pyridyldithio) propionamido] hexanoate (Sulfo-LC-SPDP) to provide efficient ways of introducing multiple sulfhydryl groups via reactive amino groups. Reactive esters, particularly N-hydroxysuccinimide (NHS) esters, are among the most commonly employed reagents for modification of amine groups. The optimum pH for reaction in an aqueous environment is pH 8.0 to 9.0. Isothiocyanates are amine-modification reagents and form thiourea bonds with proteins. They react with polypeptide amines in aqueous solution (optimally at pH 9.0 to 9.5). Aldehydes react under mild aqueous conditions with aliphatic and aromatic amines, hydrazines, and hydrazides to form an imine intermediate (Schiff's base). A Schiff's base can be selectively reduced with mild or strong reducing agents (such as sodium borohydride or sodium cyanoborohydride) to derive a stable alkyl amine bond. Other reagents that have been used to modify amines are acid anhydrides. For example, di ethyl enetriaminepentaacetic anhydride (DTPA) is a bifunctional chelating agent that contains two amine-reactive anhydride groups. It can react with N-terminal and $\epsilon$-amine groups of proteins to form amide linkages. The anhydride rings open to create multivalent, metal-chelating arms able to bind tightly to metals in a coordination complex.

Another common reactive group in polypeptides are carboxylic acids (aspartic acid, glutamic acid). Polypeptides contain carboxylic acid groups at the C-terminal position and within the side chains of aspartic acid and glutamic acid. For conjugation is the carboxylic acid group usually converted to a reactive ester by the use of a water-soluble carbodiimide and reacted with a nucleophilic reagent such as an amine, hydrazide, or hydrazine. The amine-containing reagent should be weakly basic in order to react selectively with the activated carboxylic acid in the presence of other amines on the polypeptide. Polypeptide crosslinking can occur when the pH is raised above 8.0.

Sodium periodate can be used to oxidize the alcohol part of a sugar within a carbohydrate moiety to an aldehyde. Each aldehyde group can be reacted with an amine, hydrazide, or hydrazine as described for carboxylic acids.

Thiol-reactive reagents are those that will couple to thiol groups on polypeptides, forming thioether-coupled products. These reagents react rapidly at slight acidic to neutral pH and therefore can be reacted selectively in the presence of amine groups. Haloacetyl derivatives, e.g. iodoacetamides, form thioether bonds and are reagents for thiol modification. The reaction takes place at cysteine groups that are either intrinsically present or that result from the reduction of cystine's disulfides at various positions of the polypeptide. Further useful reagents are maleimides. The reaction of maleimides with thiol-reactive reagents is essentially the same as with iodoacetamides. Maleimides react rapidly at slight acidic to neutral pH.

Amines, hydrazides, and hydrazines are aldehyde and carboxylic acid-reactive reagents (formation of amide, hydrazone, or alkyl amine bonds). Amines, hydrazides, and hydrazines can be coupled to carboxylic acids of polypeptides after the activation of the carboxyl group by a water-soluble carbodiimide. The amine-containing reagent must be weakly basic so that it reacts selectively with the carbodiimide-activated polypeptide in the presence of the more highly basic ε-amines of lysine to form a stable amide bond. In the reaction with aldehyde groups, which can be generated on polypeptides by periodate oxidation of the carbohydrate residues on the polypeptide, a Schiff's base intermediate is formed, which can be reduced to an alkyl amine through the reduction of the intermediate with sodium cyanoborohydride (mild and selective) or sodium borohydride (strong) water-soluble reducing agents.

Figure 2:
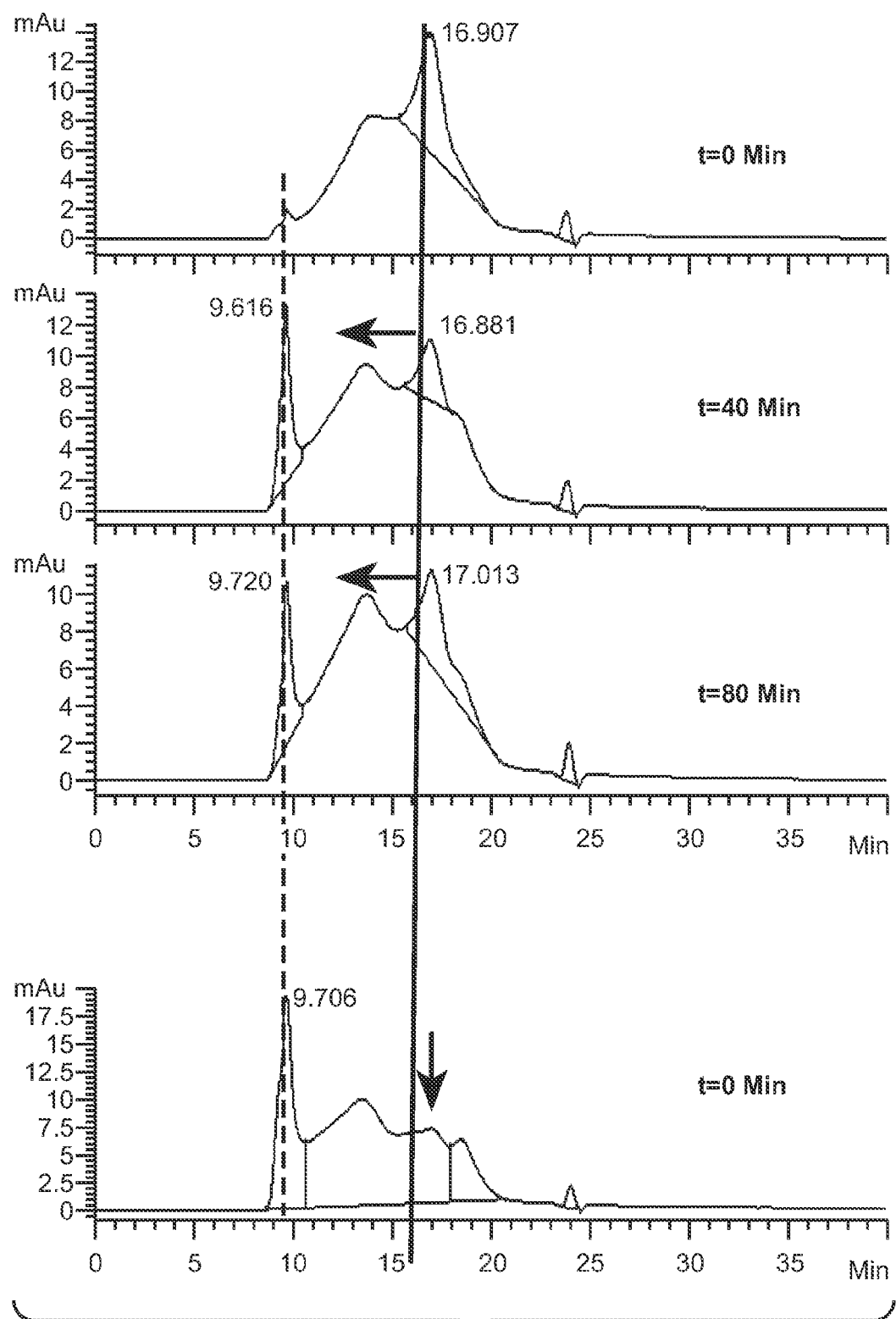
FIG. 2 Kinetic as shown in FIG. 1 with further addition of ADA.

In FIG. 1 the kinetic of a drug ADA-D complex formation is shown (1 mg drug and 1 mg ADA). It can be seen that with increasing time higher order complexes are formed, e.g. starting from a 1:1 drug:ADA-complex via a 1:2 drug:ADA complex to a 1:3 drug:ADA complex (time points 0 min., 50 min., 100 min., 160 min., 200 min.). By the addition of further ADA the composition of the sample can be further shifted to higher molecular weight complexes reducing the monomer drug peak (FIG. 2).

Figure 3:
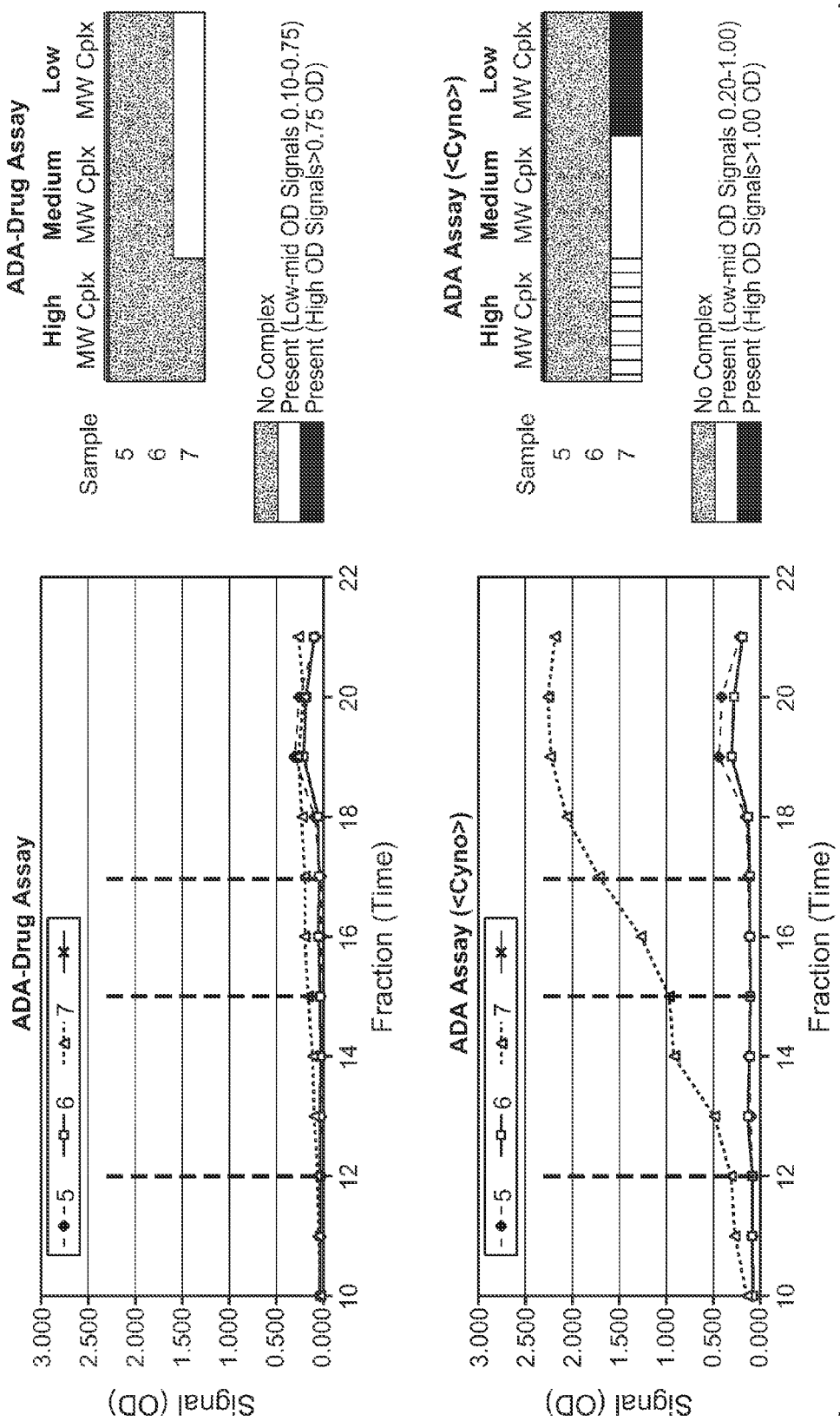
FIG. 3 Exemplary reconstituted SEC diagrams and ELISA results as obtained with the method as reported herein.
Figure 4:
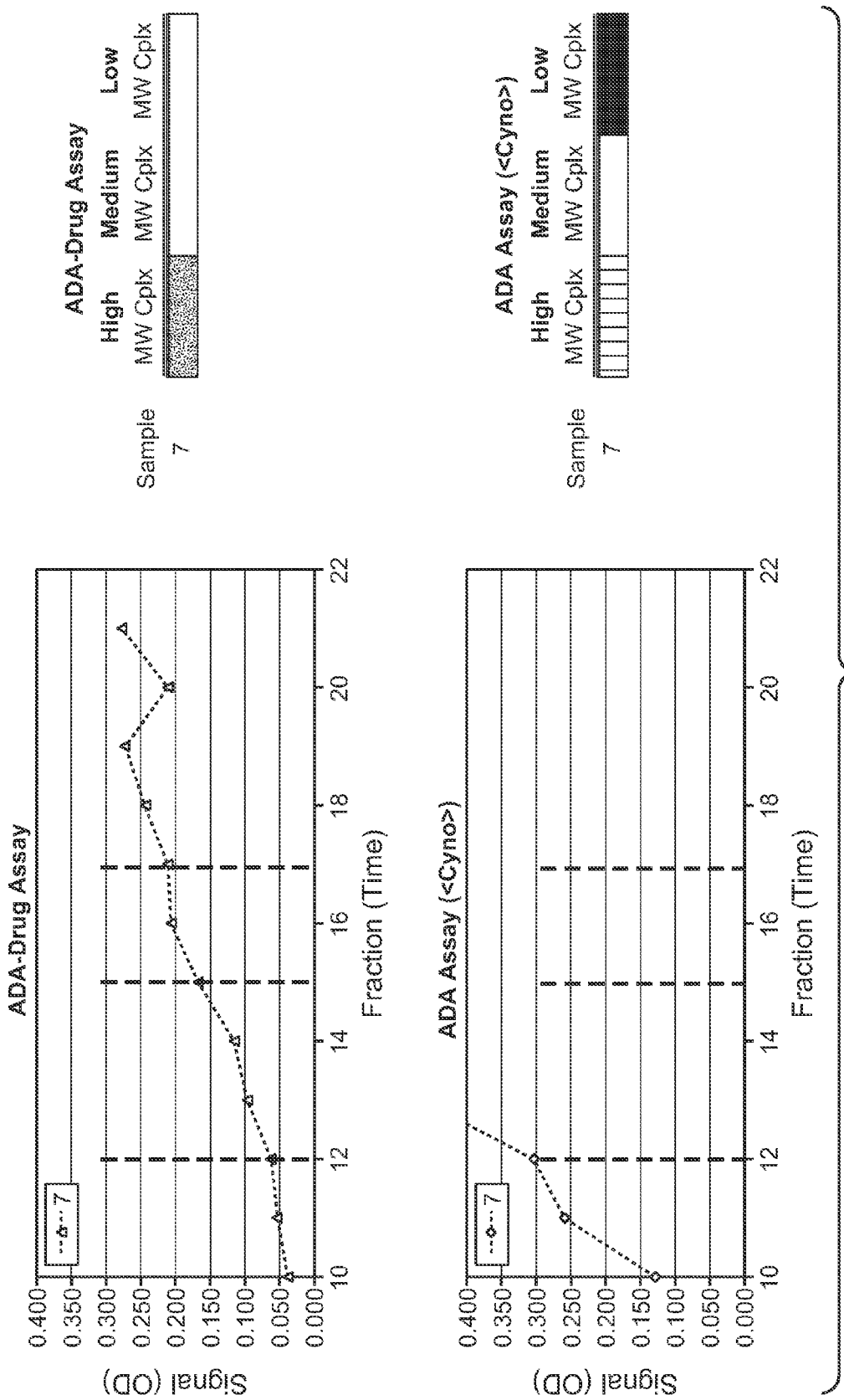
FIG. 4 Zoom of the reconstituted SEC as shown in FIG. 3.

In FIG. 3 exemplary reconstituted SEC diagrams (y-axis is OD of the ELISA) and ELISA results as obtained with the method as reported herein is shown. In FIG. 4 the zoom of the reconstituted SEC of sample 201 is shown wherein the Y-axis is kept constant. Thereby the difference in the sample composition can be seen.

The following abbreviations are used herein:
ABTS 2,2'-Azino-di-[3-ethylbenzthiazoline sulfonate (6)] di-ammonium
Ab Antibody
ADA Anti-Drug Antibodies
Bi Biotin
CoA Certificate of Analysis
Conc. Concentration
CPP Cynomolgus monkey pooled blank plasma
Dil. Dilution
ELISA Enzyme linked immunosorbent assay
HRP horseradish peroxidase
mAb Monoclonal antibody
MTP Microtiter plate
OD Optical density
PBS Phosphate buffered saline
rpm Revolutions per minute
RT Room temperature (+15 to +25° C.)
RTU Ready to use
SA Streptavidin
SEC Size exclusion chromatography The following examples are provided to aid the understanding of the present invention, the true scope of which is set forth in the appended claims. It is understood that modifications can be made in the procedures set forth without departing from the spirit of the invention.

Example 1

Analysis of Samples of a Cynomolgus Monkey Study

Twenty-seven plasma samples obtained from a cynomolgus monkey study were analyzed for detection of complexes containing anti-drug antibodies (ADA) against the administered drug. Furthermore, an assessment of complex sizes was performed.

Analysis was performed using a two-step method comprising a size-exclusion chromatography (SEC) and an enzyme linked immunosorbent assay (ELISA).

Size-dependent separation of potential complexes was achieved by SEC followed by fractionation of the SEC effluent (1 min. fractions), which enables multiplexing of the SEC analysis, since each fraction can be analyzed by different ELISAs. Detection of ADAs against the administered drug and detection of the presence of ADA-D complexes in the collected fractions was achieved by two different ELISAs. One is designed to detect ADAs (ADA assay) by using biotinylated drug for capturing and an anti-cynomolgus IgG specific detection antibody, the second assay is designed to detect ADA-D complexes, by using a drug specific capturing molecule and an anti-cynomolgus IgG specific detection antibody.

The cynomolgus plasma samples were collected from the main group and the recovery group animals. Group 1: Placebo group (samples 01, 02, 03, 04, 05, 06), group 2: basic dose (samples 07, 08, 09, 10, 11, 12), group 3: two times basic dose (samples 13, 14, 15, 16, 17, 18), group 4: four times basic dose (samples 19, 20, 21, 22, 23, 24, 25, 26, 27).

Selection of the fractionation times defines the resolution of size information. The fraction size was 1 min. The ELISA results of several fractions were combined to condense the information to "high, medium and low molecular weight fractions".

SEC:

Cynomolgus plasma samples were separated on a Bio-Suite 450, 13 µm SEC column with a molecular weight range from about 20,000 to about 7,000,000 Da. To avoid undesired precipitation of proteins on the top of the column Cynomolgus plasma was mixed with ethanol (comparable to the ethanol composition of the mobile phase) followed by a 1 min. centrifugation (ratio cynomolgus monkey plasma: ethanol (95 wt-%) about 16:1; 1 min. centrifugation at 20,800 rcf.). 20 µl sample were injected into the HPLC system (Agilent 1100). The UV trace was monitored at a wavelength of 280 nm. The isocratic separation was performed with 5% ethanol in phosphate-buffered saline (PBS) buffer as mobile phase (flow of 0.5 ml/min for 25 min. and thereafter 0.75 ml/min. for 13 minutes and 0.5 ml/min. for a final 2 minutes).

The effluent of the SEC separation was fractionated to enable detection by ELISA. In one embodiment twelve consecutive fractions with a fraction-time of 1 min were collected, covering the elution time from 9 min (void volume) to 21 min.

The calculated molecular weight corresponding to the respective fraction is given in the following table.

TABLE

| fraction | retention time [min] | molecular weight [kDa] |
| --- | --- | --- |
| 1 | 9-10 | >7000-3515 |
| 2 | 10-11 | 3515-2285 |
| 3 | 11-12 | 2285-1486 |
| 4 | 12-13 | 1486-966 |
| 5 | 13-14 | 966-628 |
| 6 | 14-15 | 628-408 |
| 7 | 15-16 | 408-265 |
| 8 | 16-17 | 265-173 |

TABLE-continued

| fraction | retention time [min] | molecular weight [kDa] |
|---|---|---|
| 9 | 17-18 | 173-112 |
| 10 | 18-19 | 112-73 |
| 11 | 19-20 | 73-47 |
| 12 | 20-21 | 47-31 |

ADA-Assays:

Detection of ADAs in higher molecular weight SEC fractions (larger than 150 kDa which is equivalent to the mass of an IgG/ADA monomer) indicates that ADA was part of a higher molecular weight complex. ADA detection is performed by analysis of the collected fraction using the ADA assay. Complex size characterization is based on SEC retention time. Complex composition characterization is achieved by analysis of the presence of ADA-D complexes (ADA-Drug complexes) in the respective fractions.

For detection of ADA and ADA-D complexes, two sequential ELISA methods have been established.

For ADA detection the wells of a SA-MTP are coated with biotinylated drug (D-Bi; c=1 μg/ml) for 1 hour. After the coating solution has been removed the wells are washed three times with 1×PBS with 0.05% Tween®20 an aliquot of the SEC-fraction is added and incubated in the MTP overnight with shaking. After washing the wells three times with 1×PBS with 0.05% Tween®20 a digoxigenylated anti-Cynomolgus Fc antibody (<Cyno Fc>-Dig, c=0.1 μg/ml) is added and incubated for one hour with shaking. After washing the wells three times with 1×PBS with 0.05% Tween®20 an anti-digoxigenin antibody conjugated to HRP (poly) Fab fragments (5 mU) is added and incubated for one hour with shaking. After washing the wells three times with 1×PBS with 0.05% Tween®20 ABTS solution is added and the color development is monitored (measuring wavelength 405 nm; reference wavelength 490 nm).

For ADA-D complex detection the wells of a SA-MTP are coated with a biotinylated anti-drug antibody (<drug>-Bi; c=2 μg/ml) for 1 hour with shaking. After the coating solution has been removed the wells are washed three times with 1×PBS with 0.05% Tween®20 an aliquot of the SEC-fraction is added and incubated in the MTP for one hour with shaking for complex detection. After the solution has been removed the wells are washed three times with 1×PBS with 0.05% Tween®20 a digoxigenylated anti-Cynomolgus Fc antibody (<Cyno-Fc>-Dig) solution is added (c=0.1 μg/ml) and incubated for 1 hour with shaking. After the solution has been removed the wells are washed three times with 1×PBS with 0.05% Tween®20 an anti-digoxygenin antibody-HRP conjugate (poly) Fab fragments solution (5 mU) is added and incubated with shaking. After washing the wells three times with 1×PBS with 0.05% Tween®20 ABTS solution is added and the color development is monitored (measuring wavelength 405 nm; reference wavelength 490 nm).

An OD signal-based cut-off value above which a SEC fraction result is defined as positive for the presence of ADA (ADA assay) or ADA-D complexes (ADA-D assay) was defined based on analysis of the study placebo samples.

The results for the ADA assay and the ADA-D assay are shown in the following table (ELISA results listed as OD values of the analysis of fractions of placebo samples (upper part: ADA Assay; lower part: ADA-D Assay)).

TABLE

| sample | fraction/retention time [mm.] | | | | | | | |
|---|---|---|---|---|---|---|---|---|
| | 9-10 | 10-11 | 11-12 | 12-13 | 13-14 | 14-15 | 15-16 | 16-17 |
| | ADA assay | | | | | | | |
| 1 | 0.07 | 0.08 | 0.09 | 0.10 | 0.11 | 0.09 | 0.10 | 0.11 |
| 2 | 0.08 | 0.13 | 0.14 | 0.13 | 0.13 | 0.13 | 0.12 | 0.14 |
| 3 | 0.10 | 0.12 | 0.12 | 0.12 | 0.12 | 0.12 | 0.12 | 0.13 |
| 4 | 0.08 | 0.08 | 0.08 | 0.10 | 0.10 | 0.10 | 0.10 | 0.12 |
| 5 | 0.08 | 0.07 | 0.09 | 0.09 | 0.10 | 0.10 | 0.10 | 0.12 |
| 6 | 0.07 | 0.07 | 0.08 | 0.12 | 0.09 | 0.10 | 0.09 | 0.11 |
| | ADA-D assay | | | | | | | |
| 1 | 0.04 | 0.03 | 0.03 | 0.04 | 0.03 | 0.03 | 0.04 | 0.04 |
| 2 | 0.04 | 0.04 | 0.05 | 0.08 | 0.05 | 0.04 | 0.05 | 0.06 |
| 3 | 0.03 | 0.04 | 0.04 | 0.04 | 0.04 | 0.04 | 0.04 | 0.04 |
| 4 | 0.03 | 0.03 | 0.03 | 0.03 | 0.03 | 0.03 | 0.03 | 0.04 |
| 5 | 0.03 | 0.03 | 0.03 | 0.03 | 0.03 | 0.03 | 0.04 | 0.04 |
| 6 | 0.04 | 0.03 | 0.03 | 0.04 | 0.04 | 0.04 | 0.04 | 0.04 |

Based on these data, a cut-off value of OD≥0.20 was defined for the ADA assay and of OD≥0.10 for the ADA-D assay, which represents about the two-fold mean blank signal in the analyzed fractions.

For further semi-quantitative evaluation, the values which are given in the following table were defined (cut-off values (OD) for the ADA-assay (left) and ADA-D assay (right)).

TABLE

| signal [OD] | result | signal [OD] | result |
|---|---|---|---|
| below 0.20 | negative | below 0.10 | negative |
| 0.20-1.00 | positive (medium signal) | 0.10-0.75 | positive (medium signal) |
| above 1.00 | positive (high signal) | above 0.75 | positive (high signal) |

Twenty-seven cynomolgus monkey plasma samples obtained from the study were analyzed for detection of complexes containing anti-drug antibodies (ADA) against the administered drug. Furthermore, an assessment of complex sizes was performed.

The results of fractions 1-3 were combined and are given as high molecular weight complex fraction, fractions 4-6 as medium molecular weight complex fraction and fractions 7-8 as low molecular weight complex fraction. Overview of the ELISA results of the analysis of fractions of the study samples is presented in the next table (left: ADA assay; right: ADA-D assay; group 1 is the placebo group; group 2 basic dose; group 3 two times basic dose; group 4 four times basic dose).

TABLE

| group | sample | ADA assay (<Cyno Fc>) | | | ADA-D assay | | |
|---|---|---|---|---|---|---|---|
| | | high MW complex | medium MW complex | low | high MW complex | medium MW complex | low |
| 1 | 1 | neg. | neg. | neg. | neg. | neg. | neg. |
| | 2 | neg. | neg. | neg. | neg. | neg. | neg. |
| | 3 | neg. | neg. | neg. | neg. | neg. | neg. |
| | 4 | neg. | neg. | neg. | neg. | neg. | neg. |
| | 5 | neg. | neg. | neg. | neg. | neg. | neg. |
| | 6 | neg. | neg. | neg. | neg. | neg. | neg. |
| 2 | 7 | neg./pos. | pos. | hpos. | neg. | pos. | pos. |
| | 8 | pos. | hpos. | hpos. | neg. | neg. | pos. |
| | 9 | pos. | pos. | pos. | neg. | neg. | neg. |
| | 10 | pos. | hpos. | hpos. | neg. | pos. | pos. |
| | 11 | pos. | hpos. | hpos. | neg. | pos. | pos. |
| | 12 | pos. | hpos. | hpos. | neg. | pos. | pos. |

TABLE-continued

| group | sample | ADA assay (<Cyno Fc>) high MW complex | ADA assay (<Cyno Fc>) medium MW complex | ADA assay (<Cyno Fc>) low MW complex | ADA-D assay high MW complex | ADA-D assay medium MW complex | ADA-D assay low MW complex |
|---|---|---|---|---|---|---|---|
| 3 | 13 | pos. | hpos. | hpos. | neg. | pos. | pos. |
|   | 14 | pos. | hpos. | hpos. | neg. | pos. | pos. |
|   | 15 | pos. | hpos. | hpos. | neg. | pos. | pos. |
|   | 16 | pos./hpos. | hpos. | hpos. | neg. | pos. | pos. |
|   | 17 | hpos. | hpos. | hpos. | neg. | pos. | pos. |
|   | 18 | hpos. | hpos. | hpos. | neg. | pos. | pos. |
| 4 | 19 | hpos. | hpos. | hpos. | pos. | pos. | hpos. |
|   | 20 | pos. | pos. | hpos. | neg. | pos. | pos. |
|   | 21 | pos. | pos. | hpos. | neg. | pos. | pos. |
|   | 22 | pos. | pos. | pos. | neg. | neg. | pos. |
|   | 23 | neg./pos. | pos. | hpos. | neg. | neg. | pos. |
|   | 24 | neg. | pos. | hpos. | neg. | neg. | neg. |
|   | 25 | pos. | hpos. | hpos. | neg. | pos. | pos. |
|   | 26 | pos. | pos. | hpos. | neg. | pos. | hpos. |
|   | 27 | neg. | pos. | hpos. | neg. | pos. | pos. | neg. = negative/below cut-off value;
pos. = positive;
hpos. = highly positive

TABLE

| group | sample | ADA assay (<Cyno Fc>) high MW complex | ADA assay (<Cyno Fc>) medium MW complex | ADA assay (<Cyno Fc>) low MW complex | ADA-D assay high MW complex | ADA-D assay medium MW complex | ADA-D assay low MW complex |
|---|---|---|---|---|---|---|---|
| 1 | 1 | − | − | − | − | − | − |
|   | 2 | − | − | − | − | − | − |
|   | 3 | − | − | − | − | − | − |
|   | 4 | − | − | − | − | − | − |
|   | 5 | − | − | − | − | − | − |
|   | 6 | − | − | − | − | − | − |
| 2 | 7 | −/+ | + | +++ | − | + | + |
|   | 8 | + | +++ | +++ | − | − | + |
|   | 9 | + | + | + | − | − | − |
|   | 10 | + | +++ | +++ | − | + | + |
|   | 11 | + | +++ | +++ | − | + | + |
|   | 12 | + | +++ | +++ | − | + | + |
| 3 | 13 | + | +++ | +++ | − | + | + |
|   | 14 | + | +++ | +++ | − | + | + |
|   | 15 | + | +++ | +++ | − | + | + |
|   | 16 | +/+++ | +++ | +++ | − | + | + |
|   | 17 | +++ | +++ | +++ | − | + | + |
|   | 18 | +++ | +++ | +++ | − | + | + |
| 4 | 19 | +++ | +++ | +++ | + | + | +++ |
|   | 20 | + | + | +++ | + | + | + |
|   | 21 | + | + | +++ | − | + | + |
|   | 22 | + | + | + | − | − | + |
|   | 23 | −/+ | + | +++ | − | − | + |
|   | 24 | − | + | +++ | − | − | − |
|   | 25 | + | +++ | +++ | − | + | + |
|   | 26 | + | + | +++ | − | + | +++ |
|   | 27 | − | + | +++ | − | + | + | signal [OD] result
− negative
+ positive (medium signal)
+++ highly positive (high signal)

Detailed ELISA results of the analysis of fractions of the study samples as shown in the previous Table is given in the next table (upper part: ADA assay; lower part: ADA-D assay; group 1 is the placebo group; group 2 basic dose; group 3 two times basic dose; group 4 four times basic dose).

TABLE

| | | ADA assay (<Cyno Fc>) | | | | | | | |
|---|---|---|---|---|---|---|---|---|---|
| group | sample | fraction 1 high MW complex fraction | fraction 2 high MW complex fraction | fraction 3 high MW complex fraction | fraction 4 medium MW complex fraction | fraction 5 medium MW complex fraction | fraction 6 medium MW complex fraction | fraction 7 medium MW complex fraction | fraction 8 medium MW complex fraction |
| 1 | 1 | 0.074 | 0.083 | 0.091 | 0.097 | 0.105 | 0.094 | 0.098 | 0.111 |
|   | 2 | 0.081 | 0.125 | 0.145 | 0.132 | 0.125 | 0.130 | 0.121 | 0.141 |
|   | 3 | 0.103 | 0.119 | 0.122 | 0.123 | 0.120 | 0.120 | 0.123 | 0.130 |
|   | 4 | 0.081 | 0.079 | 0.085 | 0.098 | 0.098 | 0.099 | 0.104 | 0.117 |
|   | 5 | 0.076 | 0.075 | 0.085 | 0.090 | 0.099 | 0.097 | 0.100 | 0.120 |
|   | 6 | 0.067 | 0.068 | 0.075 | 0.121 | 0.091 | 0.104 | 0.092 | 0.108 |
| 2 | 7 | 0.129 | 0.259 | 0.303 | 0.470 | 0.899 | 0.959 | 1.259 | 1.710 |
|   | 8 | 0.516 | 0.674 | 0.667 | 0.712 | 0.836 | 1.282 | 1.539 | 1.899 |
|   | 9 | 0.753 | 0.656 | 0.656 | 0.579 | 0.618 | 0.735 | 0.819 | 0.963 |
|   | 10 | 0.618 | 0.672 | 0.644 | 0.959 | 1.255 | 1.360 | 1.664 | 1.844 |
|   | 11 | 0.307 | 0.328 | 0.312 | 0.633 | 1.115 | 1.674 | 1.986 | 2.119 |
|   | 12 | 0.467 | 0.536 | 0.622 | 0.840 | 1.228 | 1.449 | 1.723 | 1.266 |
| 3 | 13 | 0.656 | 0.604 | 0.692 | 0.833 | 1.344 | 1.701 | 2.127 | 2.337 |
|   | 14 | 0.577 | 0.774 | 0.482 | 0.911 | 1.101 | 1.422 | 1.877 | 2.072 |
|   | 15 | 0.595 | 0.612 | 0.555 | 0.944 | 1.277 | 1.886 | 2.169 | 2.170 |
|   | 16 | 0.440 | 0.808 | 1.116 | 1.573 | 1.826 | 1.891 | 1.955 | 2.022 |
|   | 17 | 1.610 | 1.562 | 1.521 | 1.544 | 1.617 | 1.672 | 1.844 | 2.029 |
|   | 18 | 1.232 | 1.324 | 1.239 | 1.378 | 1.447 | 1.711 | 1.878 | 1.941 |
| 4 | 19 | 1.251 | 1.485 | 1.552 | 1.645 | 1.696 | 1.783 | 1.894 | 1.984 |
|   | 20 | 0.268 | 0.390 | 0.392 | 0.495 | 0.484 | 0.795 | 1.639 | 2.118 |
|   | 21 | 0.253 | 0.423 | 0.450 | 0.528 | 0.629 | 0.999 | 1.518 | 2.210 |
|   | 22 | 0.236 | 0.233 | 0.214 | 0.222 | 0.228 | 0.259 | 0.317 | 0.550 |
|   | 23 | 0.158 | 0.198 | 0.220 | 0.250 | 0.288 | 0.466 | 0.884 | 1.860 |
|   | 24 | 0.023 | 0.048 | 0.081 | 0.124 | 0.231 | 0.457 | 0.826 | 1.294 |
|   | 25 | 0.383 | 0.776 | 0.891 | 0.896 | 0.946 | 1.170 | 1.649 | 2.013 |
|   | 26 | 0.173 | 0.272 | 0.265 | 0.289 | 0.409 | 0.692 | 1.214 | 1.999 |
|   | 27 | 0.128 | 0.167 | 0.204 | 0.187 | 0.228 | 0.345 | 0.559 | 1.127 |

TABLE

| | | ADA-D assay | | | | | | | |
|---|---|---|---|---|---|---|---|---|---|
| group | sample | fraction 1 high MW complex fraction | fraction 2 high MW complex fraction | fraction 3 high MW complex fraction | fraction 4 medium MW complex fraction | fraction 5 medium MW complex fraction | fraction 6 medium MW complex fraction | fraction 7 medium MW complex fraction | fraction 8 medium MW complex fraction |
| 1 | 1 | 0.035 | 0.034 | 0.031 | 0.037 | 0.035 | 0.034 | 0.039 | 0.043 |
|   | 2 | 0.036 | 0.041 | 0.051 | 0.077 | 0.053 | 0.043 | 0.048 | 0.056 |
|   | 3 | 0.035 | 0.038 | 0.037 | 0.044 | 0.040 | 0.039 | 0.041 | 0.043 |
|   | 4 | 0.028 | 0.029 | 0.029 | 0.034 | 0.030 | 0.030 | 0.034 | 0.036 |
|   | 5 | 0.028 | 0.029 | 0.027 | 0.032 | 0.031 | 0.032 | 0.036 | 0.038 |
|   | 6 | 0.035 | 0.034 | 0.033 | 0.040 | 0.036 | 0.036 | 0.044 | 0.044 |
| 2 | 7 | 0.038 | 0.053 | 0.060 | 0.097 | 0.116 | 0.166 | 0.206 | 0.211 |
|   | 8 | 0.033 | 0.038 | 0.035 | 0.042 | 0.048 | 0.064 | 0.097 | 0.123 |
|   | 9 | 0.035 | 0.042 | 0.038 | 0.049 | 0.046 | 0.051 | 0.068 | 0.085 |
|   | 10 | 0.037 | 0.048 | 0.057 | 0.168 | 0.199 | 0.155 | 0.163 | 0.155 |
|   | 11 | 0.051 | 0.064 | 0.065 | 0.089 | 0.139 | 0.246 | 0.322 | 0.376 |
|   | 12 | 0.032 | 0.037 | 0.044 | 0.071 | 0.097 | 0.134 | 0.156 | 0.154 |
| 3 | 13 | 0.052 | 0.060 | 0.069 | 0.111 | 0.185 | 0.388 | 0.478 | 0.436 |
|   | 14 | 0.036 | 0.042 | 0.050 | 0.075 | 0.133 | 0.244 | 0.339 | 0.460 |
|   | 15 | 0.047 | 0.052 | 0.060 | 0.104 | 0.174 | 0.386 | 0.673 | 0.549 |
|   | 16 | 0.043 | 0.055 | 0.061 | 0.096 | 0.158 | 0.258 | 0.358 | 0.518 |
|   | 17 | 0.052 | 0.056 | 0.058 | 0.073 | 0.077 | 0.140 | 0.217 | 0.178 |
|   | 18 | 0.034 | 0.042 | 0.043 | 0.059 | 0.071 | 0.136 | 0.176 | 0.207 |
| 4 | 19 | 0.073 | 0.122 | 0.144 | 0.186 | 0.236 | 0.417 | 0.820 | 0.748 |
|   | 20 | 0.333 | 0.392 | 0.364 | 0.371 | 0.358 | 0.374 | 0.435 | 0.431 |
|   | 21 | 0.044 | 0.063 | 0.066 | 0.079 | 0.099 | 0.165 | 0.315 | 0.457 |
|   | 22 | 0.044 | 0.050 | 0.052 | 0.061 | 0.061 | 0.070 | 0.092 | 0.137 |
|   | 23 | 0.036 | 0.040 | 0.044 | 0.054 | 0.062 | 0.100 | 0.206 | 0.290 |
|   | 24 | 0.031 | 0.033 | 0.032 | 0.037 | 0.038 | 0.044 | 0.058 | 0.074 |
|   | 25 | 0.047 | 0.055 | 0.060 | 0.100 | 0.116 | 0.108 | 0.151 | 0.188 |
|   | 26 | 0.040 | 0.055 | 0.055 | 0.074 | 0.119 | 0.256 | 1.574 | 2.739 |
|   | 27 | 0.085 | 0.082 | 0.084 | 0.095 | 0.114 | 0.176 | 0.298 | 0.380 |

ADAs against the drug could be detected in all analyzed samples of treated animals (group 2-4). Differences between the samples are observed with regard to signal intensity as well as with regard to positivity in high molecular weight fractions.

Negative results were observed in certain fractions of the following samples: sample 7/fraction1; sample 23/fraction 1-2, sample 24/fraction1-4; sample 26/fraction1; sample 27/fraction1-3.

ADA-D complexes could be detected in all but two samples (sample 10, 24) of treated animals. Differences between the samples are observed with regard to signal intensity. With the exception of sample 19 and sample 20, all samples showed negative results in the high molecular weight fractions (fractions 1-3).

Example 2

Correlation of SEC-ELISA Analysis and Pharmacokinetics

Five cynomolgus plasma samples were collected pre-dosing and at the following time points, day=9, 13, 21, 23 (all samples) and at day=63 (animal 2004, 2005, 3002, 3105) and were analyzed for detection of complexes containing anti-drug antibodies (ADA) against the administered drug. Furthermore, an assessment of complex sizes with the observed pharmacokinetic of the administered drug was performed.

Analysis was performed using a two-step method comprising a size-exclusion chromatography (SEC) and an enzyme linked immunosorbent assay (ADA-D assay and ADA assay) as reported in Example 1. For the correlation with the pharmacokinetic of the administered drug, only the results of the ADA-D assay were used.

The cynomolgus plasma samples were collected from five cynomolgae with a dosing of the drug of 100 mg/kg.

Figure 5:
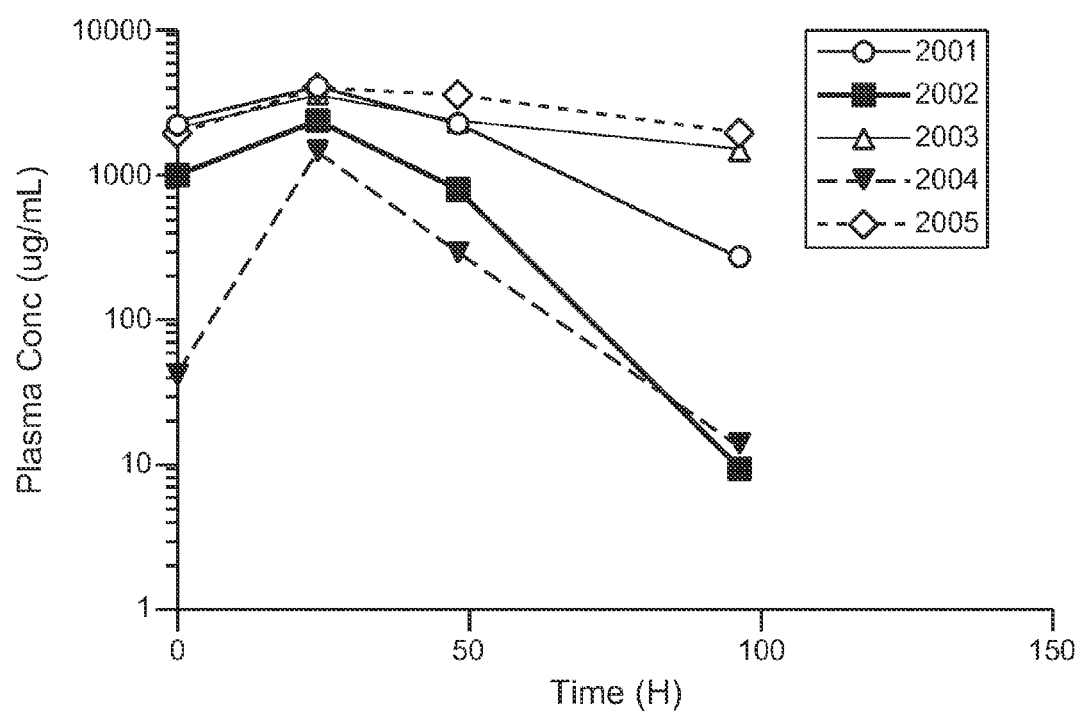
FIG. 5 Concentration course of applied drug in the plasma of five monkeys (dose=100 mg/kg, repeated application, applied at day 17 of the study).

From plasma analysis it can be seen that in the cynomolgae number 2001, 2002 and 2004 a more rapid serum clearance compared to cynomolgae number 2003 and 2005 could be observed (see FIG. 5).

The effluent of the SEC separation was fractionated with a fraction-time of 1 min, covering the elution time from 9 min (void volume) to 21 min. The calculated molecular weight corresponding to the respective fraction is used as described in Example 1 above.

An OD signal-based cut-off value above which a SEC fraction result is defined as positive for the presence of ADA (ADA assay) or ADA-D complexes (ADA-D assay) was defined based on analysis of the pre-dose samples of the study animals.

The results for the ADA assay and the ADA-D assay are shown in the following table (ELISA results listed as OD values of the analysis of fractions of placebo samples (upper part: ADA Assay; lower part: ADA-D Assay)).

| | | ADA-assay fraction/retention time [min.] | | | | | | | |
|---|---|---|---|---|---|---|---|---|---|
| ape no | time | 9-10 | 10-11 | 11-12 | 12-13 | 13-14 | 14-15 | 15-16 | 16-17 |
| 2001 | t = 0 | 0.031 | 0.032 | 0.031 | 0.036 | 0.039 | 0.042 | 0.043 | 0.045 |
| | t = 9 d | 0.043 | 0.053 | 0.050 | 0.049 | 0.051 | 0.050 | 0.053 | 0.052 |
| | t = 13 d | 0.140 | 0.129 | 0.103 | 0.085 | 0.091 | 0.099 | 0.093 | 0.092 |
| | t = 21 d | 0.471 | 0.566 | 0.557 | 0.691 | 0.898 | 1.064 | 1.419 | 1.497 |
| | t = 23 d | 0.284 | 0.461 | 0.470 | 0.803 | 1.539 | 1.906 | 2.039 | 2.113 |
| 2002 | t = 0 | 0.032 | 0.040 | 0.035 | 0.043 | 0.045 | 0.050 | 0.055 | 0.053 |
| | t = 9 d | 0.043 | 0.044 | 0.041 | 0.044 | 0.049 | 0.049 | 0.049 | 0.054 |
| | t = 13 d | 0.116 | 0.98 | 0.085 | 0.083 | 0.083 | 0.117 | 0.083 | 0.065 |
| | t = 21 d | 1.259 | 1.506 | 1.627 | 1.840 | 1.932 | 1.909 | 2.009 | 2.010 |
| | t = 23 d | 0.185 | 0.401 | 0.945 | 1.573 | 1.991 | 2.106 | 2.205 | 2.149 |
| 2003 | t = 0 | 0.035 | 0.040 | 0.034 | 0.035 | 0.038 | 0.042 | 0.054 | 0.067 |
| | t = 9 d | 0.040 | 0.040 | 0.037 | 0.042 | 0.045 | 0.042 | 0.055 | 0.071 |
| | t = 13 d | 0.046 | 0.045 | 0.060 | 0.089 | 0.107 | 0.146 | 0.188 | 0.299 |
| | t = 21 d | 0.191 | 0.150 | 0.123 | 0.125 | 0.175 | 0.177 | 0.167 | 0.423 |
| | t = 23 d | 0.097 | 0.180 | 0.551 | 1.393 | 1.622 | 1.915 | 1.939 | 1.969 |
| 2004 | t = 0 | 0.042 | 0.050 | 0.042 | 0.042 | 0.044 | 0.050 | 0.069 | 0.121 |
| | t = 9 d | 0.043 | 0.053 | 0.054 | 0.054 | 0.054 | 0.050 | 0.070 | 0.108 |
| | t = 13 d | 0.106 | 0.120 | 0.218 | 0.693 | 1.250 | 1.512 | 1.429 | 1.781 |
| | t = 21 d | 0.774 | 0.679 | 0.842 | 0.812 | 1.304 | 1.724 | 1.998 | 2.273 |
| | t = 23 d | 0.253 | 0.338 | 0.375 | 0.763 | 1.500 | 1.769 | 2.020 | 2.176 |
| | t = 63 d | 0.059 | 0.063 | 0.067 | 0.086 | 0.090 | 0.108 | 0.223 | 0.870 |
| 2005 | t = 0 | 0.046 | 0.054 | 0.047 | 0.050 | 0.056 | 0.062 | 0.067 | 0.075 |
| | t = 9 d | 0.045 | 0.054 | 0.050 | 0.053 | 0.053 | 0.048 | 0.047 | 0.053 |
| | t = 13 d | 0.046 | 0.068 | 0.061 | 0.065 | 0.056 | 0.064 | 0.060 | 0.067 |
| | t = 21 d | 1.769 | 1.524 | 1.823 | 1.256 | 1.294 | 1.312 | 1.572 | 1.393 |
| | t = 23 d | 0.136 | 0.144 | 0.199 | 0.608 | 0.867 | 1.111 | 1.387 | 1.471 |
| | t = 63 d | 0.604 | 0.635 | 0.811 | 0.552 | 0.444 | 0.573 | 0.477 | 0.791 |

| | | ADA-D-assay fraction/retention time [min.] | | | | | | | |
|---|---|---|---|---|---|---|---|---|---|
| ape no | time | 9-10 | 10-11 | 11-12 | 12-13 | 13-14 | 14-15 | 15-16 | 16-17 |
| 2001 | t = 0 | 0.074 | 0.086 | 0.074 | 0.083 | 0.094 | 0.100 | 0.097 | 0.102 |
| | t = 9 d | 0.059 | 0.105 | 0.092 | 0.087 | 0.084 | 0.084 | 0.088 | 0.087 |
| | t = 13 d | 0.561 | 0.563 | 0.268 | 0.183 | 0.103 | 0.086 | 0.081 | 0.088 |
| | t = 21 d | 0.121 | 0.127 | 0.124 | 0.143 | 0.163 | 0.187 | 0.247 | 0.258 |
| | t = 23 d | 0.136 | 0.160 | 0.222 | 0.572 | 1.481 | 2.156 | 1.896 | 1.247 |
| 2002 | t = 0 | 0.087 | 0.094 | 0.076 | 0.085 | 0.089 | 0.097 | 0.102 | 0.088 |
| | t = 9 d | 0.061 | 0.081 | 0.077 | 0.076 | 0.073 | 0.072 | 0.078 | 0.079 |
| | t = 13 d | 0.644 | 0.364 | 0.223 | 0.149 | 0.125 | 0.092 | 0.080 | 0.082 |
| | t = 21 d | 0.174 | 0.187 | 0.198 | 0.253 | 0.285 | 0.300 | 0.392 | 0.422 |
| | t = 23 d | 0.062 | 0.090 | 0.152 | 0.369 | 0.725 | 1.116 | 1.141 | 0.476 |
| 2003 | t = 0 | 0.078 | 0.086 | 0.068 | 0.069 | 0.070 | 0.076 | 0.088 | 0.116 |
| | t = 9 d | 0.055 | 0.066 | 0.065 | 0.070 | 0.068 | 0.071 | 0.092 | 0.135 |
| | t = 13 d | 0.068 | 0.065 | 0.063 | 0.065 | 0.065 | 0.069 | 0.079 | 0.113 |
| | t = 21 d | 0.361 | 0.331 | 0.253 | 0.227 | 0.207 | 0.274 | 0.296 | 0.328 |
| | t = 23 d | 0.416 | 0.412 | 0.476 | 0.605 | 0.410 | 0.365 | 0.256 | 0.301 |
| 2004 | t = 0 | 0.086 | 0.110 | 0.083 | 0.090 | 0.086 | 0.091 | 0.121 | 0.217 |
| | t = 9 d | 0.067 | 0.119 | 0.111 | 0.111 | 0.100 | 0.098 | 0.136 | 0.220 |
| | t = 13 d | 0.168 | 0.156 | 0.245 | 0.359 | 0.264 | 0.224 | 0.200 | 0.294 |
| | t = 21 d | 0.129 | 0.167 | 0.256 | 0.174 | 0.191 | 0.242 | 0.403 | 0.605 |
| | t = 23 d | 0.082 | 0.095 | 0.107 | 0.208 | 0.483 | 1.070 | 1.820 | 1.490 |
| | t = 63 d | 0.036 | 0.036 | 0.038 | 0.047 | 0.046 | 0.046 | 0.056 | 0.098 |
| 2005 | t = 0 | 0.046 | 0.057 | 0.057 | 0.065 | 0.075 | 0.082 | 0.093 | 0.110 |
| | t = 9 d | 0.081 | 0.116 | 0.114 | 0.109 | 0.103 | 0.097 | 0.099 | 0.113 |
| | t = 13 d | 0.142 | 0.206 | 0.163 | 0.173 | 0.165 | 0.165 | 0.182 | 0.165 |
| | t = 21 d | 0.307 | 0.291 | 0.262 | 0.269 | 0.269 | 0.258 | 0.303 | 0.276 |
| | t = 23 d | 0.217 | 0.213 | 0.215 | 0.236 | 0.178 | 0.143 | 0.136 | 0.139 |
| | t = 63 d | 0.036 | 0.039 | 0.036 | 0.041 | 0.040 | 0.043 | 0.046 | 0.055 |

| | | OD correlations | | | |
|---|---|---|---|---|---|
| | | ADA-assay | | ADA-D-assay | |
| ape no | time | sum of OD | OD sum (all days without pre-dose and day 63) | sum of OD | OD sum (all days without pre-dose and day 63) |
| 2001 | t = 0 | 0.297 | 18.0 | 0.708 | 11.9 |
| | t = 9 d | 0.400 | | 0.685 | |
| | t = 13 d | 0.830 | | 1.932 | |
| | t = 21 d | 7.161 | | 1.369 | |
| | t = 23 d | 9.614 | | 7.868 | |
| 2002 | t = 0 | 0.352 | 26.7 | 0.716 | 8.7 |
| | t = 9 d | 0.371 | | 0.594 | |
| | t = 13 d | 0.729 | | 1.756 | |
| | t = 21 d | 14.090 | | 2.210 | |
| | t = 23 d | 11.552 | | 4.129 | |

TABLE-continued

OD correlations

| | | ADA-assay | | ADA-D-assay | |
|---|---|---|---|---|---|
| ape no | time | sum of OD | OD sum (all days without pre-dose and day 63) | sum of OD | OD sum (all days without pre-dose and day 63) |
| 2003 | t = 0 | 0.344 | 12.5 | 0.648 | 6.7 |
| | t = 9 d | 0.370 | | 0.620 | |
| | t = 13 d | 0.977 | | 0.584 | |
| | t = 21 d | 1.529 | | 2.275 | |
| | t = 23 d | 9.664 | | 3.240 | |
| 2004 | t = 0 | 0.457 | 27.2 | 0.883 | 10.3 |
| | t = 9 d | 0.484 | | 0.960 | |
| | t = 13 d | 7.107 | | 1.909 | |
| | t = 21 d | 10.404 | | 2.065 | |
| | t = 23 d | 9.139 | | 5.353 | |
| | t = 63 d | 1.565 | | 0.401 | |
| 2005 | t = 0 | 0.456 | 18.7 | 0.584 | 5.9 |
| | t = 9 d | 0.402 | | 0.830 | |
| | t = 13 d | 0.485 | | 1.360 | |
| | t = 21 d | 11.942 | | 2.234 | |
| | t = 23 d | 5.920 | | 1.475 | |
| | t = 63 d | 4.885 | | 0.333 | |

| | | ADA-assay | | ADA-D-assay | |
|---|---|---|---|---|---|
| ape no | time | sum of OD | ODsum (all days without pre-dose and day 63) | sum of OD | OD sum (all days without pre-dose and day 63) |
| 2005 | t = 0 | 0.456 | 18.7 | 0.584 | 5.9 |
| | t = 9 d | 0.402 | | 0.830 | |
| | t = 13 d | 0.485 | | 1.360 | |
| | t = 21 d | 11.942 | | 2.234 | |
| | t = 23 d | 5.920 | | 1.475 | |
| | t = 63 d | 4.885 | | 0.333 | |

From FIG. 5 it can be seen that enhanced clearance is observed for animal 2001, 2002 and 2004. For these animals the obtained OD sum (all days without pre-dose and day 63) signals of the ADA-D assay are 11.9 (animal 2001), 8.7 (animal 2002) and 10.3 (animal 2004). These signals are clear above the signals of 6.7 (animal 2003) and 5.9 (animal 2004) which did not show enhanced clearance. Thus, increasing amounts of ADA-Drug complexes indicate for a faster plasma clearance.

Example 3

Correlation of SEC-ELISA Analysis and IgG Glomerula Deposit Findings

For each assay (ADA-Assay and ADA-D-Assay) at t=21d and t=23d and each dosing group (Group A and Group B) the signals of the fractions of the retention time blocks 9 min. to 12 min. (block 1), 12 min. to 15 min. (block 2) and 15 min. to 17 min. (block 3) are summarized (see tables below for ADA-D-Assay and ADA-Assay).

TABLE

ADA-D-assay

| ape no/ Group | time | block 1 | block 2 | block 3 |
|---|---|---|---|---|
| 2001/A | t = 21 d | 0.372 | 0.492 | 0.505 |
| | t = 23 d | 0.517 | 4.209 | 3.143 |

TABLE-continued

ADA-D-assay

| ape no/ Group | time | block 1 | block 2 | block 3 |
|---|---|---|---|---|
| 2002/A | t = 21 d | 0.558 | 0.838 | 0.814 |
| | t = 23 d | 0.303 | 2.210 | 1.616 |
| 2003/A | t = 21 d | 0.944 | 0.708 | 0.624 |
| | t = 23 d | 1.304 | 1.380 | 0.557 |
| 3001/B | t = 21 d | 0.491 | 0.542 | 0.562 |
| | t = 23 d | 1.966 | 4.988 | 1.652 |
| 3003/B | t = 21 d | 0.585 | 0.801 | 0.907 |
| | t = 23 d | 0.512 | 2.324 | 3.595 |
| 3004/B | t = 21 d | 0.522 | 0.522 | 0.446 |
| | t = 23 d | 0.493 | 1.378 | 1.944 |

TABLE

ADA-assay

| ape no/ Group | time | block 1 | block 2 | block 3 |
|---|---|---|---|---|
| 2001/A | t = 21 d | 1.593 | 2.652 | 2.916 |
| | t = 23 d | 1.215 | 4.248 | 4.152 |
| 2002/A | t = 21 d | 4.392 | 5.681 | 4.018 |
| | t = 23 d | 1.530 | 5.669 | 4.353 |
| 2003/A | t = 21 d | 0.464 | 0.476 | 0.589 |
| | t = 23 d | 0.827 | 4.930 | 3.908 |
| 3001/B | t = 21 d | 3.111 | 3.303 | 2.554 |
| | t = 23 d | 1.195 | 4.746 | 4.253 |
| 3003/B | t = 21 d | 4.174 | 4.654 | 4.352 |
| | t = 23 d | 0.882 | 3.242 | 4.170 |
| 3004/B | t = 21 d | 3.616 | 3.783 | 3.396 |
| | t = 23 d | 0.574 | 1.870 | 3.900 |

The summed signals obtained for the time point t=23d is divided by the signal obtained for the time point t=21d ("quotient 1") to indicate a loss or rise of signal at t=23d.

TABLE

Quotient 1 ( d23/d21)

| ape no/ Group | block 1 ADA-D | block 2 ADA-D | block 3 ADA-D | block 1 ADA | block 2 ADA | block 3 ADA |
|---|---|---|---|---|---|---|
| 2001/A | 1.390 | 8.554 | 6.229 | 0.762 | 1.602 | 1.424 |
| 2002/A | 0.543 | 2.638 | 1.985 | 0.348 | 0.998 | 1.083 |
| 2003/A | 1.382 | 1.950 | 0.892 | 1.784 | 10.356 | 6.634 |
| 3001/B | 4.003 | 9.211 | 2.941 | 0.384 | 1.437 | 1.665 |
| 3003/B | 0.876 | 2.903 | 3.966 | 0.211 | 0.697 | 0.958 |
| 3004/B | 0.945 | 2.642 | 4.358 | 0.159 | 0.494 | 1.148 |

The "quotient 1" values of the ADA-D-Assay are divided by the "quotient 1" values of the ADA-Assay to obtain the "quotient 2" values. High "quotient 2" values in block 1 (e.g. above 2 or 3) indicate glomerular deposits in the animals.

TABLE

Quotient 2 (ADA-D/ADA)

| ape no/ Group | block 1 | block 2 | block 3 |
|---|---|---|---|
| 2001/A | 1.823 | 5.341 | 4.374 |
| 2002/A | 1.559 | 2.644 | 1.832 |
| 2003/A | 0.774 | 0.188 | 0.134 |
| 3001/B | 10.421 | 6.411 | 1.766 |
| 3003/B | 4.145 | 4.168 | 4.139 |
| 3004/B | 5.955 | 5.346 | 3.795 |

In addition, the "quotient 2" values of each dosing group and block are statistically tested by F-test and T-test (alfa 5%) to differentiate whether the values/mean of block 1 to block 3 of the groups are different or not.

TABLE

Average of quotient 2

| Group | block 1 | block 2 | block 3 |
|---|---|---|---|
| A | 1.385 | 2.724 | 2.114 |
| B | 6.840 | 5.308 | 3.233 |
| Statistically difference A to B | Yes | No | No |

The glomerular deposit data are ranked in "−" for no deposits over "(+)" for slightly visible glomerular deposits to "+" and "++" for positive samples with a semi-quantitative differentiation of the found glomerular deposits in the animals.

TABLE

Glomerular deposits

| ape no/Group | IgG IF Glomerular deposits |
|---|---|
| 2001/A | − |
| 2002/A | (+) |
| 2003/A | − |
| 3001/B | + |
| 3003/B | ++ |
| 3004/B | ++ |

The results listed in the tables above show a correlation of the SEC separated immune complexes to glomerular deposits of the animals. High values in block 1 indicate glomerular deposits in the animals. All animals of Group A are ranked as "−" and "(+)" and all animals of group B are ranked as "+" and "++". The mean values of these groups are statistically different.

As shown in the "Glomerular deposits" table, a semi-quantitative differentiation between the IgG glomerular deposit result was observed, with animals 3003 and 3004 showing more pronounced deposits.

As shown in the tables for the ADA-Drug assay and the ADA-assay the sum of the signals in block 1 are indirectly proportional with the glomerula deposits results (see also FIG. 6).

The invention claimed is:

1. A method for determining the size of an anti-drug antibody complexed with an exogenous therapeutic polypeptide drug (ADA-D complex) comprising
   a) a size-exclusion chromatography ("SEC") of a sample from a mammal to which a synthetic or non-naturally occurring therapeutic polypeptide drug had been administered at least once for determining the weight/size of the ADA-D complex, wherein an eluate of the SEC is collected in fractions,
   b) at least one heterogeneous immunoassay of each fraction of the eluate collected in the SEC for detecting the anti-drug antibody of the ADA-D complex, and
   c) determining the weight/size of the ADA-D complex, by determining which fraction of the eluate of the SEC contains ADA-D as determined by the heterogeneous immunoassays of step (b) and correlating the weight/size of the ADA-D with the fractions of the eluate in which the ADA-D complex is detected,
   whereby the ADA-D complex is characterized to be
   a low molecular weight complex between about 150 kDa and about 400 kDa,
   a medium molecular weight complex between about 400 kDa and about 1,500 kDa, or
   a high molecular weight complex between about 1,500 kDa and about 7,000 kDa.

2. The method according to claim 1, wherein the sample is serum or cerebrospinal fluid.

3. The method according to claim 1 or 2, characterized in that at least one of the fractions of the size-exclusion chromatography is further separated by a second non-SEC chromatography with collection of the eluate in fractions.

4. The method according to claim 1 or 2, wherein the immunoassay is an anti-drug antibody immunoassay.

5. The method according to claim 1 or 2, wherein at least one of the immunoassays is a bridging enzyme linked immunosorbent assay.

6. The method according to claim 1 or 2, wherein at least one of the immunoassays is a complex assay for the detection of the ADA-D complex.

7. The method according to claim 6, wherein the complex assay comprises a drug specific capture antibody and an anti-species specific antibody as detection antibody.

8. The method according to claim 1 or 2, wherein at least one of the immunoassays is a direct assay for the detection of anti-drug antibodies which are bound to the drug and/or to an endogenous counterpart of the drug.

9. The method according to claim 8, wherein the direct assay comprises as capture molecule immobilized drug or endogenous counterpart of the drug and an anti-species specific antibody as detection antibody.

10. The method of claim 1, further comprising a mass-spectrometry-based analysis of at least one fraction of the eluate collected in the SEC to further characterize the ADA-D complex.

11. The method of claim 1, wherein individual fractions of the eluate of the size exclusion chromatography are analyzed using a second-dimension chromatography to determine the charge of the ADA-D complex.

12. The method of claim 1, wherein individual fractions of the eluate of the size exclusion chromatography are analyzed by reversed phase chromatography or hydrophilic interaction chromatography to determine the polarity of the ADA-D complex.

* * * * *